(12) United States Patent
Van Der Giessen et al.

(10) Patent No.: US 7,470,441 B2
(45) Date of Patent: Dec. 30, 2008

(54) **METHOD FOR PREPARING *MUCUNA PRURIENS* SEED EXTRACT**

(75) Inventors: Rob Van Der Giessen, Aesch (CH); C. Warren Olanow, Rye, NY (US); Andrew Lees, London (GB); Hildebert Wagner, Breitbrunn (DE)

(73) Assignee: Phytrix AG, Munich (DE)

( * ) Notice: Subject to any disclaimer, the term of this patent is extended or adjusted under 35 U.S.C. 154(b) by 0 days.

(21) Appl. No.: 10/533,135

(22) PCT Filed: Oct. 2, 2003

(86) PCT No.: PCT/EP03/10975

§ 371 (c)(1),
(2), (4) Date: Nov. 18, 2005

(87) PCT Pub. No.: WO2004/039385

PCT Pub. Date: May 13, 2004

(65) Prior Publication Data

US 2006/0165822 A1    Jul. 27, 2006

(30) Foreign Application Priority Data

Oct. 30, 2002    (EP) ................... 02024475

(51) Int. Cl.
*A61K 36/48*    (2006.01)
(52) U.S. Cl. ..................................... 424/757
(58) Field of Classification Search ............. None
See application file for complete search history.

(56) References Cited

U.S. PATENT DOCUMENTS 3,941,835 A * 3/1976 Riccardi ..................... 562/446
6,106,839 A * 8/2000 Pruthi et al. ................ 424/734
2002/0166182 A1 * 11/2002 Bhagyalakshmi et al. ...... 8/405

OTHER PUBLICATIONS

1996. Mahajami et al. Bioavailability of L-DOPA from HP-200- a formulation of seed powder of *Mucuna pruriens* (Bak): a Pharmacokinteic and Pharmacodynamic Study. Phytotherapy Research, vol. 10, 254-256.*
1997. Hussain et al. *Mucuna pruriens* proves more effective than L-DOPA in Parkinson's disease animal model. Phytotherapy Research, vol. 11, 419-423.*
2002. Tripathi et al. Effect of the alcohol extract of the seeds of *Mucuna pruriens* on free radicals and oxidative stress in albino rats. Phytotherapy Research. 16. 534-538.*
1937. Damodaran et al. Isolation of 3,4-dihydroxyphenylalanine from the seeds of *Mucuna pruriens*. Biochemistry. 31. 2149-21512.*
1954. Majumdar et al. *Mucuna pruriens* IV. Alkaloidal consituents and their derivatives. Indian Pharmacist. vol. 10 p. 79-84.*
wikipedia.org.*
2002. Vickers et al. Drugs Aging. 19 (7): 487-494.*

* cited by examiner

*Primary Examiner*—Patricia Leith
*Assistant Examiner*—Melenie McCormick
(74) *Attorney, Agent, or Firm*—Baker Botts L.L.P.

(57) ABSTRACT

The present invention provides pharmaceutical compositions comprising *Mucuna pruriens* seeds or one or more *Mucuna pruriens* seed components, substances, fractions or mixtures or substances obtained therefrom. Furthermore, the invention relates to the use of *Mucuna pruriens* seed powder or one or more *Mucuna pruriens* components, substances, fractions or mixtures or substances obtained therefrom for the preparation of a pharmaceutical composition for preventing, alleviating or treating neurological diseases. Additionally, the invention relates to the use of *Mucuna pruriens* seeds for the preparation of a pharmaceutical composition for neuroprotection or neurostimulation and to methods of preparing extracts of *Mucuna pruriens* which can be used for the preparation of a pharmaceutical composition for treating neurological diseases. Finally, the invention relates to the use of *Mucuna pruriens* seeds for the preparation of a pharmaceutical composition for the treatment of Parkinson's Disease to obtain a broader therapeutic window in L-Dopa therapy, to delay a need for combination therapy, to obtain an earlier onset and longer duration of L-Dopa efficacy, and to prevent or alleviate acute and chronic L-Dopa toxicity.

7 Claims, 3 Drawing Sheets

METHOD FOR PREPARING *MUCUNA PRURIENS* SEED EXTRACT

Figure 1:
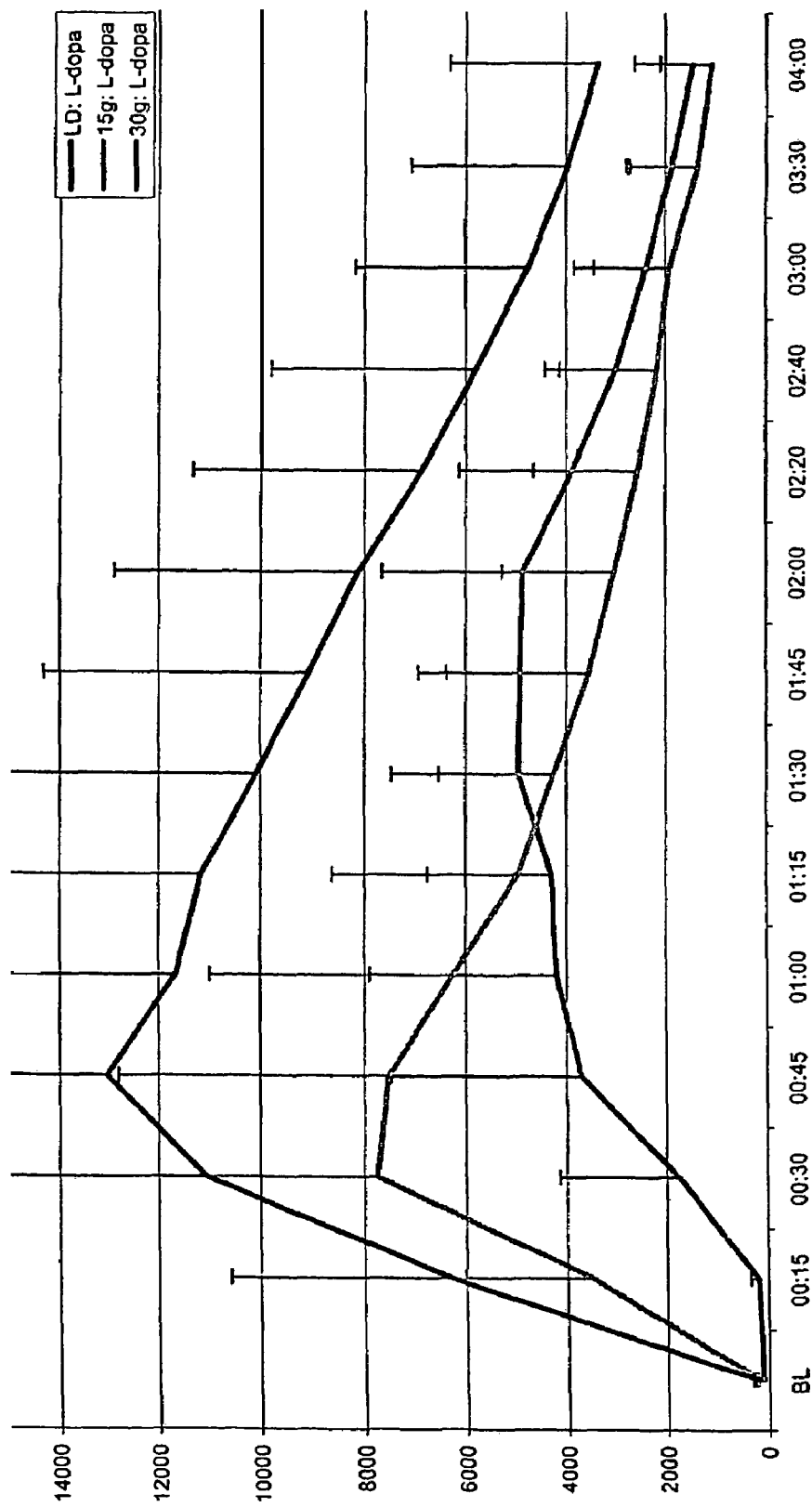

The present invention provides pharmaceutical compositions comprising *Mucuna pruriens* seeds or one or more *Mucuna pruriens* seed components, substances, fractions or mixtures or substances obtained therefrom. Furthermore, the invention relates to the use of *Mucuna pruriens* seedpowder or one or more *Mucuna pruriens* components, substances, fractions or mixtures or substances obtained therefrom for the preparation of a pharmaceutical composition for preventing, alleviating or treating neurological diseases. Additionally, the invention relates to the use of *Mucuna pruriens* seeds for the preparation of a pharmaceutical composition for neuroprotection or neurostimulation and to methods of preparing extracts of *Mucuna pruriens* which can be used for the preparation, of a pharmaceutical composition for treating neurological diseases.

Several documents are cited throughout the text of this specification. The disclosure content of the documents cited herein (including any manufacture's specifications, instructions, etc.) is herewith incorporated by reference.

A large number of neurological and neurological degenerative disease are known, many of which are presently not curable. These diseases comprise medical conditions such as Parkinson's disease, Chorea Huntington, Hallervorder-Spatz disease, Alzheimer's disease, senile dementia, Creutzfeldt-Jakob disease, artheriosclerotic dementia, cerebral thrombangitis obliterans and many others. Parkinson's disease (PD) is a progressive movement and age-related disorder that is estimated to affect for example more than 500,000 persons in the United States, with as many as 50,000 new cases each year, at an estimated cost of 27 billion dollars annually. Usually PD begins in a person's late 50s or early 60s, it causes a progressive decline in movement control, affecting the ability to control initiation, speed and smoothness of motion. Symptoms of PD are seen in up to 15% of those between the ages 65 to 74, and almost 30% of those between the ages of 75 and 84. PD is one of the best characterized diseases of the basal ganglia. The symptoms that come along with the disease are a rhythmical tremor at rest, a unique increase in muscle tone or rigidity that has often cogwheel- or ratchet-like characteristic, difficulty in the initiation of movement and paucity of spontaneous movements (akinesia), and slowness in the execution of movement (bradykinesia). In humans suffering from Parkinson's disease dopamine is missing or most drastically reduced in certain regions of the brain which are essentially needed, for example, for controlling the movement of the body. L-DOPA is metabolised within the body to dopamine which plays an outstanding role in the metabolism of the brain as neurotransmitter.

Beside the reduction of dopamine which coincides with the symptoms of the disease, it is also speculated that the destruction of dopamine-producing nerve cells especially those of the substantia nigra pars compacta in the mid brain (one of the principal movement control centers in the brain) contributes to the disease. This control center helps to refine movement patterns throughout the body. It was observed that the brains of patients with Parkinson's disease also have loss of nerve cells and depigmentation in the two pigmented loci of the brain stem: the substantia nigra and the locus ceruleus. Thereby, the severity of changes in the substantia nigra parallels the reduction of dopamine in the striatum. Because the pars compacta of the substantia nigra contains many of the dopaminergic nerve cell bodies in the brain, these observations suggest that the dopaminergic pathway from the substantia nigra to the striatum is disturbed in Parkinson's disease. However, the molecular mechanisms underlying PD are still under investigation and poorly understood.

From the above-mentioned findings that brains of PD patients have a drastically reduced dopamine level, it was reasoned that they might be helped if the amount of dopamine in the brain were restored to normal. Therefore, among others, L-3,4-hydroxyphenylalanine (L-DOPA), also known a levodopa, was administered intravenously to patients. L-DOPA, as the immediate precursor of dopamine is, in contrast to dopamine, capable of crossing the blood-brain barrier. After the prolonged administration, a remarkable but brief remission in the patient's symptoms was observed which suggested an approach for the treatment of Parkinson's disease. However, this effect is generally associated with long term side effects and disease progression is not prevented. The reason for the strong side effect observed during treatment with levodopa is not known but suggests a toxic effect of said compound or its metabolites, including dopamine. Furthermore, it has been postulated that L-Dopa and its metabolite dopamine themselves have a toxic effect on neural-tissues and thus, besides alleviating the disease symptoms, may contribute to disease progression. It is important to note that Dopamine does not pass the blood-brain barrier in sufficient quantities, thus only a small percentage of L-Dopa reaches the brain after systemic administration. Moreover, L-Dopa is quickly metabolised peripherally, therefore high systemic L-Dopa doses are required to achieve the clinical effect (3-4 gr. L-Dopa/day). In view of the fact that immediate side-effects are directly related to L-Dopa peak plasma levels, L-Dopa was, in recent years, administered in combination therapy with other compounds such as decarboxylase and COMT (Catechol-amine-O-methyl-transferase) inhibitors to prevent peripheral metabolisation. To prevent the metabolisation of dopamine in the brain, MAO (Mono-amine oxidase) inhibitors were also used. With these additives it was possible to reduce the daily required dose of L-Dopa to an average of about 600 mg/day. However, these additives were only partially capable of reducing the toxic side effects of the treatment with levodopa and could not prevent disease progression. Thus, there was an urgent need for an effective treatment of Parkinson's disease and other levodopa-sensitive neurological diseases which is not associated with or counteracting the side-effects of L-Dopa therapy including neurotoxicity.

Thus, the technical problem underlying the present invention was to provide means and methods for treating neurological diseases including Parkinson's disease.

The solution to this technical problem is achieved by providing the embodiments characterized in the claims.

Accordingly, the present invention relates to a pharmaceutical composition comprising *Mucuna pruriens* seed powder or one or more components, substances, fractions or mixtures of substances obtained therefrom and a pharmaceutically acceptable diluent, excipient or carrier.

*Mucuna pruriens* is a plant of the family Leguminoseae and is indigenous to tropical countries like India and West Indies. It is an annual, climbing leguminous vine capable of growing to 6 m in length. The lanceolate leaves are alternate with three large, rhomboid-ovate leaflets. The flowers grow in racemes in 2 or 3 and are white to dark purple and hang in long racemes. *Mucuna pruriens* produces clusters of pods that are curved (4 to 8 cm long) and contain 2 to 6 seeds. The seeds vary in colour from black, white to mottled. The pods which are thick and leathery are covered with reddish-orange long stiff hairs that are readily dislodged and can cause intense irritation to the skin.

Since *Mucuna pruriens* and its use is so widespread that it is considered common fare from China to England, Iran to Spain, Africa to South America, it has a variety of common names like Nescafe, Cowage, Velvetbean, Fagiolo Di Rio Negro, Fogarate, Jeukerwt, Juckbohne, Nd, Pien Tou, Pois A Gatter, Pois Gratte, Swagupta, T'Ao Hung King, Kekara gatel or Rarawejah.

Velevetbean, a vigorous annual climbing legume, originally came from southern China and eastern India, where it was at one time widely cultivated as a green vegetable crop. The genus *Mucuna,* belonging to the Fabaceae family, covers perhaps 100 species of annual and perennial legumes, including the annual velvetbean.

According to Dr. Duke's Phytochemical and Ethnobotanical Databases at phytochemical Database, USDA-ARS-NGRL, Beltsville Agricultural Research Center, Beltsville, Md. *Mucuna pruriens* contains many diverse Phytochemicals like 1-methyl-3-carboxy-6,7-dihydroxy-1 2,3,4-tetrahydroisoquinolone, 5-hydroxytryptamine, 5-methoxy-n,n-dimethyltryptamine-n-oxide, 5-oxyindole-3-alkylamine, 6-methoxyharman, Alanine, Arachidic-acid, Arginine, Aspartic-acid, Behenic-acid, Beta-carboline, Beta-sitosterol, Bufotenine, Choline, Cis-12,13-epoxyoctadec-trans-9-cis-acid, Cis-12,13-epoxyoctadec-trans-9-enoic-acid, Cystine, DOPA, Gallic-acid, Glutamic-acid, Glutathione, Glycine, Histidine, L-DOPA, Lecithin, Leucine, Linoleic-acid, Mucunadine, Mucunain, Mucunine, Myristic-acid, N,n-dimethyltryptamine, N,n-dimethyltryptamine-n-oxide, Nicotine, Oleic-acid, Palmitic-acid, Palmitoleic-acid, Phenyalanine, Phosphorus, Proline, Protein, Prurienidine, Prurienine, Saponins, Serine, Serotonin, Stearic-acid, Threonine, Tryptamine, Tyrosine, Valine, Vernolic-acid. Therefore, *Mucuna pruriens* finds traditionally use in a number of diseases and is commonly used as carminative, hypotensive & hypoglycemnic agent. Moreover it is also used as anodyne, antidotal, aphrodisiac, diuretic, nervine, resolvent, rubefacient, and vermifuge; used for anasarca, asthma, cancer, cholera, cough, diarrhea, dogbite, dropsy, dysuria, insanity, mumps, pleuritis, ringworm, snakebite, sores, syphilis, tumors, and worms.

From phytochemistry point of view, the drug contains dimethyltryptamine alkaloids and related alkaloids, lecithin and tannins as well as L-DOPA, a precursor of the neural transmitter dopamine. All these compounds are known to exist in the seeds of *Mucuna pruriens.* Therefore, plants like *Mucuna pruriens* provide a natural source for drugs for Parkinson's disease since they contain, among many other phytochemicals, large amounts of levodopa (L-DOPA).

The term "therapeutically effective" means in an amount sufficient to prevent, treat or ameliorate a disease or the symptoms associated with a disease. The term "obtained" means isolated, extracted or otherwise taken or gained from the seed. The person skilled in the art knows various techniques for isolating or obtaining compounds from plants, some of which are described below.

The term "pharmaceutically acceptable" means approved by a national regulatory agency or by a generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and, oils, including those of petroleum, animal, vegetable or synthetic origin, such as peanut oil, soybean oil, mineral oil sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

The terms "components", "substances", "fractions" or "mixtures of substances" all refer to compounds or mixtures of compounds isolated from *Mucuna pruriens* seeds. The term "isolated" refers to the process of obtaining or isolating the compound. The isolated component may initially be present in a crude extract of the seed, together with many other components of the seed. Later stages of the extraction process will yield fractions containing a reduced variety of components. This mixture of components may have similar physical or chemical properties. Further fractionation, however, will ultimately result in the complete isolation of a single molecular species which is the isolated component. The term "substance" as used herein refers to the isolated or pure component. However, methods such as solvent extraction generally result in a final fraction which contains minute amounts of contaminants. Preferably the substance is 100% pure, less preferably the substance is at least 99%, 98%, 97%, 96%, 95%, 94%, 93%, 92%, 80% or at least 70% pure. However, in certain cases also substances with a smaller degree of purity can be therapeutically effective. Therefore, the invention also refers to substances which are only at least 60%, 55% or even 50% pure.

The pharmaceutical composition, *Mucuna pruriens* seed powder or extracts, disclosed by the present invention allow long term L-Dopa treatment of neurological diseases, including Parkinson's Disease, in the absence of the short- and long term side effects observed in conventional treatment approaches. The term *"Mucuna pruriens* seed powder" relates to powder prepared from the seeds of *Mucuna pruriens*. Powder of *Mucuna pruriens* seeds can be prepared from dried beans which are freed from their cutular hairs by a brushing machine, then milled in a special mill for herbal drugs. The resulting powder is passed through a standard sieve No. 4 or 5, corresponding to a mesh width of 850 or 355 µm. The pharmaceutical composition and specific extracts of the present invention, not containing L-Dopa, can be applied as such for the treatment of neurodegenerative diseases in general, or in combination with isolated L-Dopa if required.

Conventional L-Dopa therapy requires a gradual increase of the effective dose over time resulting of progression of disease and/or the neurotoxic effects of L-Dopa or dopamine with an increase of toxic reactions and, over time, the appearance of dyskinesia, increasing in severity with dose. In clinical experiences with *Mucuna prurience* seed preparations these negative phenomena have not been observed in that for the effective treatment of Parkinson's, the dose of *Mucuna pruriens* derived L-Dopa remained relatively stable over longer periods of time, and in that dyskinesia, even in patients with pre-existing dyskinesia following long term therapy with conventional L-Dopa preparations, appeared to be less in occurrence and severity.

The present invention represents a rationale for this experience. Surprisingly, even in cases of relatively high levels of L-Dopa in blood following *Mucuna pruriens* administration, no immediate toxic effects were encountered normally to be expected with such levels following administration of conventional preparations.

The clinical study presented in the Examples of the present invention demonstrates that this seed powder formulation of *Mucuna pruriens* contains a considerable quantity of L-Dopa which is sufficient to consistently induce a sustained on-period in fluctuating patients with short duration L-Dopa response. The quality of motor improvement following a single dose challenge was equivalent to that seen with synthetic LD/DC. Both with the dose of 15 g and 30 g *Mucuna pruriens* the time to the beginning of switching "on" and the time to the full "on"-state was significantly shorter than with a pharmaceutical composition containing a combination of synthetic L-Dopa and decarboxylase inhibitor (LD/DC). The duration of the on-period was significantly longer with 30 g *Mucuna pruriens* than with LD/DC. This was reflected in the pharmacokinetic profile of L-Dopa plasma levels, showing a significantly steeper slope of increase and earlier $T_{max}$ for *Mucuna pruriens* and larger total AUCs. For.30 g *Mucuna* both the early onset and long duration of effect can in part be explained by the early and higher peak dose levels and the large AUC after ingestion of this dose. Although not significant, the duration of effect of the 15 g *Mucuna* dose tended to be somewhat shorter than with LD/DC. This is reflected in the pharmacokinetic findings in that the L-Dopa level following this dose decreased below the level of LD/DC after about 1.5 hours. In a clinical setting this could therefore be corrected with a dose adaptation.

These findings raise the possibility that *Mucuna pruriens* formulations may actually have a faster bioavailability than standard L-Dopa preparations. This is likely to be related to differences in the speed of gastrointestinal absorption of L-Dopa from the duodenum. The most obvious differences between the *Mucuna* preparation and the synthetic formulation used in this study was the administration of *Mucuna* as a suspension as opposed to a capsule, and the addition of a peripheral decarboxylase inhibitor to the standard L-Dopa preparation.

Decarboxylase inhibitors mainly increase L-Dopa plasma levels by blocking the peripheral degradation of L-Dopa to dopamine, thus allowing more L-Dopa to cross the blood-brain barrier with an exogenous L-Dopa dose reduction of 60-80% (14-17). However, one of the sites for decarboxylation of oral L-Dopa is the gastric and intestinal mucosa (18), and decarboxylase inhibitors have been reported to enhance intestinal L-Dopa absorption (19,20), presumably by inhibiting metabolic pathways such as aromatic dehydroxylation in the gut. Other studies confirmed that, in the presence of a decarboxylase inhibitor, peak L-Dopa concentrations were higher and were reached more rapidly (14, 21, 22).

Figure 2:
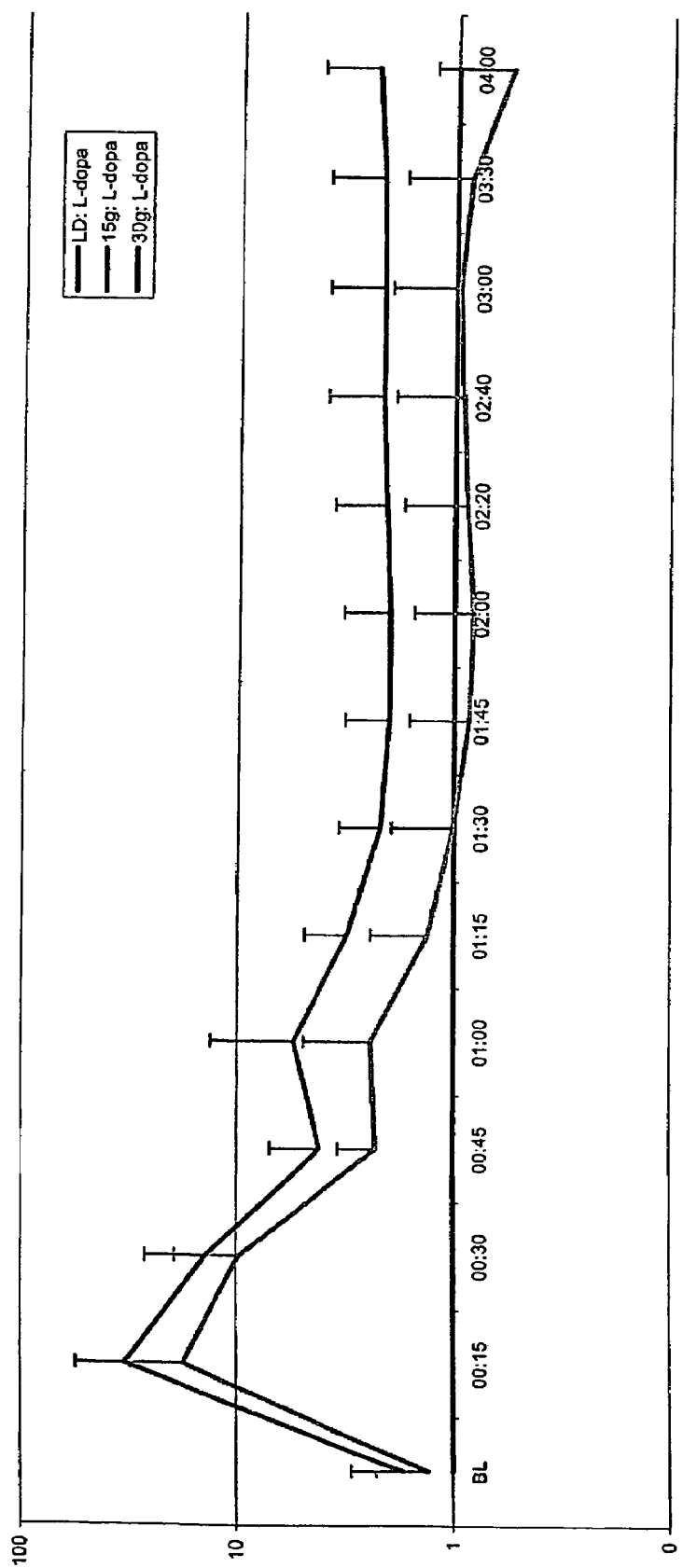

In the light of these reports, the observations in the underlying study are surprising. A possible explanation for this may lie in the administration of *Mucuna* as a suspension. On the other hand, the L-Dopa in the *Mucuna* seed powder is embedded in organic material. Although it can not be excluded, it is unlikely that its liberation is so much quicker than the disintegration of a gelatine capsule in the gastric fluid to be a sufficient explanation for such marked differences in pharmacokinetics. Additives contained in the *Mucuna* powder formulation may also have had an impact on absorption: A small amount of ascorbic acid and citric acid, added for chemical stability (23), may potentially have improved intestinal absorption (24). The small amounts actually added to the formulation (0.188 g/unit) do not seem to be a sufficient explanation however. Furthermore, in a previous clinical trial using a *Mucuna pruriens* formulation not containing such additives the $C_{max}$ of L-Dopa also appeared to be reached within 1 hour (5). Decarboxylase inhibitors have been shown to prolong L-Dopa half life (21,22,25). Although the decline of L-Dopa plasma levels on 15 g *Mucuna* was slightly, but not significantly, faster than on LD/DC, the L-Dopa levels on 30 g *Mucuna* declined at the same rate as with LD/DC as shown in the intrapatient analysis (FIG. 2). Therefore it is feasible that in addition to L-Dopa *Mucuna pruriens* seed powder contains an absorption enhancing and potentially also a decarboxylase inhibitor-like factor.

Another surprising finding was that in spite of a much higher L-Dopa exposure on the *Mucuna* preparations the 3-OMD plasma levels did not increase accordingly. In fact there was no significant difference in 3-OMD levels on 30 g *Mucuna* (with a 159% higher LD AUC) compared with the levels on LD/DC. Furthermore, on 15 g *Mucuna* (LD AUC 31% higher) there was a steady decline of 3-OMD levels reaching a significant difference with LD/DC (p=0.009 at 240 minutes). If no decarboxylase inhibitor-like factor is present in *Mucuna* seed powder this could be explained by a predominantly metabolisation of L-Dopa by decarboxylation. Otherwise a doses dependent COMT-like inhibition of dopamine metabolism by another factor contained in *Mucuna pruriens* seed powder could play a role in addition.

*Mucuna pruriens* seed powder is a natural plant product and therefore by definition contains more chemical substances besides L-Dopa. Therefore, and in view of the results of our study, further investigations into factors potentially promoting gastrointestinal absorption of L-Dopa and altering its metabolism are warranted.

Tolerability was comparable in all study drugs. All adverse events that occurred were mild and short-lasting. Acute side effects of L-Dopa such as nausea, vomiting, and orthostatic hypotension (dizziness) have been shown to be correlated with plasma levels (26). In view of the significantly higher plasma levels reached on *Mucuna* than on LD:DC, it is remarkable that side effect profiles were similar in this single dose challenging study. In fact, but not significantly due to patient numbers, the number of events on *Mucuna* was lower compared with LD/DC.

In addition, the results of the AIMS and Goetz scores indicate, that in spite of the significantly higher L-Dopa plasma levels on *Mucuna,* dyskinesias were not increased on *Mucuna* compared with LD/DC (27). Furthermore, the Dyskinesia Motor Index even indicates a dose dependent decrease in the index. This decrease did not reach significance in this single dose challenge study, however, due to small patient numbers, but seems to corroborate earlier clinical observations.

*Mucuna pruriens* contains larger amounts of L-Dopa than any other known natural source (28,29). The clinical data summarized above shows that L-Dopa uptake is considerably increased. It could therefore be postulated that this *Mucuna pruriens* may also produce factors to protect vulnerable cells against oxidative damage. In fact, the experiments performed in connection with the present invention demonstrate a neuroprotective and neurostimulatory property of *Mucuna pruriens.*

In order to characterize the active components in *Mucuna pruriens* and possibly to identify the factors responsible for the increased uptake of dopamine and to characterize the neuroprotective properties of *Mucuna pruriens,* a number of in vitro experiments were performed. Initially, the effect of *Mucuna pruriens* fractions on primary dopaminergic cultures was tested resulting in the identification of two fractions significantly increasing dopamine uptake. In another set of experiments, fractions of *Mucuna pruriens* extracts were tested with respect for their potential to reduce toxic effects of MPP and BSO. The results of these experiments allowed the identification of fractions, containing a neuroprotective factor of *Mucuna pruriens.* In addition, the experiments demonstrate that other fractions contain factors that increase cellular uptake of dopamine.

Based on this preliminary single dose, double blinded, double dummy challenging study in patients with Parkinson's Disease and short duration of L-Dopa response, the *Mucuna pruriens* formulation seems to possess potential advantages over existing commercially available synthetic L-Dopa formulations in that it combines a rapid onset of action with a comparable or longer duration of therapeutic response without increasing dyskinesias or acute LD toxicity in spite of much higher LD plasma levels. If better tolerability of L-Dopa can be confirmed in further pre-clinical and larger and longer term clinical studies, *Mucuna pruriens* would provide a wider therapeutic index for L-Dopa treatment for PD patients and thus be a viable alternative to standard synthetic L-Dopa formulations.

In a preferred embodiment, the components, substances, fractions or mixtures of substances are extracted from *Mucuna pruriens* seeds.

The term "extraction" refers to the process of obtaining or isolating a compound from *Mucuna pruriens* seeds. The person skilled in the art knows of various extraction techniques all of which rely on the physical properties of the compounds to be isolated. Extraction, as used herein, relates to the separation of medicinally active portions of *Mucuna pruriens* from the inactive or inert components through the use of selective solvents. The person skilled in the art knows that the term "extraction" comprises maceration, percolation, digestion, infusion and decoction. Many extraction methods contain one or more steps of mechanical treatment of the seed which is usually an initial step that may be followed by a filtration, a washing and/or a drying step. The extraction protocol may be composed of several extraction steps, resulting in the generation of one or more fractions containing various concentrations of the therapeutically active compound. However, methods such as solvent extraction generally result in a final, fraction which contains minute amounts of contaminants. Preferably the substance is 100% pure, less preferably the substance is at least 99%, 98%, 97%, 96%, 95%, 94%, 93%, 92%, 80% or at least 70% pure. However, in certain cases also substances with a smaller degree of purity can be therapeutically effective. Therefore, the invention also refers to substances which are only at least 60%, 55% or even 50% pure. When the extraction protocol comprises more than one extraction step, the extraction steps may be followed or preceded by additional steps of pre-treatment. These pre-treatments may be important in order to optimise the quality and/or quantity of the next extraction process and may include steps such as mixing, heat-treatment, addition of chemical compounds, filtration, distillation.

In a preferred embodiment, the pharmaceuutical composition comprise bipolar-lipophilic molecules obtained by extraction of *Mucuna pruriens.*

Solvent extraction relies on differential solvent solubility of the seed components. Polar solvents will tend to extract water-soluble compounds, non-polar solvents will tend to extract lipophilic compounds, while amphiphilic solvents can extract lipophilic as well as water-soluble compounds. The person skilled in the art knows of various solvents that can be used in an extraction process. Preferably the solvent used is a single solvent selected from the group consisting of water, hexane, acetone, ethanol, chloroform, ethylacetate, diclormethane and petrolether. However, also preferred are mixtures of two or more solvents. The solvent may additionally contain compounds such as enzyme inhibitors including phosphatase inhibitors or protease inhibitors, reducing or oxidizing agents or the like including DTT, GSH, ascorbic acid or $SO_2$-gas, chelating agents including EGTA or EDTA, and mono- or divalent ions including $Mg^{2+}$, $Ca^{2+}$, $Na^+$, $Li^+$, $Cl^-$, $SO_4^2$, $K^+$, $NO_3$. These additional compounds present in the solvent or added after extraction may be important to preserve the physical state of the therapeutically active compound. Another preferred embodiment is extraction in the presence of gases such as nitrogen or argon which may also be important for controlling the oxidative state of the extract.

Physical parameters such as pressure or temperature may play an important role for extraction procedures since they can have a strong impact on the state of aggregation of the seed components or of the solvent. High pressure, e.g., results in liquefaction of carbon dioxide and other gases and may have a strong impact on the result of the extraction process. Carbon dioxide, e.g. is known to be an excellent solvent at hypercritical conditions. Methods of extracting plant material, including methods of extraction with hypercritical $CO_2$, are known in the art (Verdichtete Gase zur Extraktion and Raffinierung, E. Stahl, Springer Verlag, Heidelberg, Berlin, 1986). Accordingly, the extraction process of the present invention may be performed at low pressure, i.e. at low pressure: <200 bar, intermediate pressure: 200-300 bar, high pressure: >300 bar. Similarly, the temperature during the extraction process can be important for the yield of the extraction process. Accordingly the present invention can be performed at low temperature, i.e. between 0° C. and 10° C., at an intermediate temperature, i.e. between 10° C. and 40° C., preferably 20° C., 25° C., 30° C. or 37° C., or at high temperature, i.e. between 40° C. and 100° C.

Accordingly, the present invention relates in a preferred embodiment to a method for the preparation of extracts or extract fractions of *Mucuna pruriens,* comprising extracting the seed of *Mucuna pruriens* with $CO_2$ or mixtures from $CO_2$ and butane, propane or other gases under supercritical conditions or different pressures and temperatures, to obtain purification and selection of substances or fractionation of *Mucuna pruriens* extracts.

In a preferred embodiment of the present invention, *Mucuna pruriens* seeds or seed powder is extracted twice with acetone. The remaining material is further extracted with n-propanol.

In another preferred embodiment of the present invention, *Mucuna pruriens* seeds or seed powder is extracted at least one time with a 1:1 mixture of water and ethanol. The extraction process can be performed in the presence or absence of ascorbic acid. In another preferred embodiment of the present invention, *Mucuna pruriens* seeds or seed powder is initially extracted by water, the resulting extract is further fractionated by ethanol precipitation.

In a more preferred embodiment, the components, substances, fractions or mixtures of substances are extracted from *Mucuna pruriens* seeds by using bipolar-lipophilic solvent molecules such as acetone, DMSO or dimethylformamide which extract lipophilic and a great part of polar of hydrophilic substances from the plant material. These solvents are sometimes also designated simply as bipolar. Other extraction methods are staggered procedures starting with organic solvents followed by polar solvents or vice versa. Very often also water-alcohol, alcohol-acetone or acetone-hexane solvent mixtures are used to extract lipophilic and hydrophilic constitutents in one extraction operation. Preferably the bipolar-lipophilic solvent is selected from the group consisting of acetone, DMSO or dimethylformamide. However, this list is non-limiting and the person skilled in the art knows of many other bipolar-lipophilic molecules which might be used in the extraction process.

In another preferred embodiment, the pharmaceutical composition is formulated as an infusion, an injection solution, a gelatin-capsule, a tablet or a controlled release tablet. Many delivery systems are known to the person skilled in the art and can be used to administer a compound of the invention, e.g., encapsulation in liposomes, microparticles, microcapsules. Methods of introduction include but, are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent, it may be desirable to administer the pharmaceutical compounds or compositions of the invention locally to the area in need of treatment. The compound or composition can be delivered in a vesicle, in particular a liposome (see Langer, Science 249: 1527-1533 (1990); Treat et al., in Liposomes in the Therapy of Infectious Diseases and Cancer, Lopez-Berestein and Fidler (eds.), Liss, N.Y., pp. 353-365 (1989); Lopez-Berestein, ibid., pp. 317-327; see: generally ibid.). The compound or composition can be delivered in a controlled release system, including the use of a pump (see Langer, supra; Sefton, CRC Crit. Ref. Biomed. Eng. 14:201 (1987); Buchwald et al., Surgery 88:507 (1980); Saudek et al., N. Engl. J. Med. 321: 574 (1989)). The above-mentioned controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

In another preferred embodiment, the present invention's pharmaceutical composition comprises (a) a neurostimulatory extract of *Mucuna pruriens* selected from the group consisting of M-PL0100, M-EL100, M-BL0100 and LAT543-0 or (b) a neuroprotective extract of *Mucuna pruriens* selected from the group consisting of M-W-EL1299, M-W0100, MWEL0700 and M-ML0100. One or more of the extracts may be combined in the same pharmaceutical composition.

The term "M-PL0100" refers to an extract obtainable, from *Mucuna pruriens* by shaking 10 g of the pulverised seeds of *M. pruriens*, preferably for 18 hours at room temperature, in n-propanol (50 ml) and by filtering subsequently. The extraction of the residue may be followed by one, two or more additional steps of shaking with n-propanol and filtering. The filtrates may be pooled together and the solvent distilled off to get an oily mass. Of course, larger or smaller quantities of M-PL0100 can be prepared, simply by reducing or increasing the amount of seeds and solvent.

The term "M-EL100" refers to an extract obtainable from *Mucuna pruriens* by shaking 20 g of pulverised seeds of *M. pruriens*, preferably for 18 hours, in EtOH (100 ml). After filtration, the residue is shaken, preferably for 18 hours, and filtered. The process may be repeated two, three, four or up to ten times. Subsequently, the filtrates may be concentrated and pooled together to get the extract. Of course, larger or smaller quantities of M-EL100 can be prepared, simply by reducing or increasing the amount of seeds and solvent.

The term "M-BL0100" relates to an extract obtainable from *Mucuna pruriens* by shaking 10 g of pulverised seeds of *M. pruriens*, preferably for 18 hours at room temperature in n-butanol (50 ml). Preferably a step of filtering follows. Subsequently, the residue may be extracted two or more times with n-butanol, preferably followed by a step of filtering. The filtrates may be pooled together and the solvent distilled off. The oily extract is thus obtained. Of course, larger or smaller quantities of M-BL0100 can be prepared, simply by reducing or increasing the amount of seeds and solvent.

The term "LAT00270543" is defined as "LAT543" and the term "LAT00270543-0" is defined as "LAT543-0". Both LAT543 and LAT543-0 are polysaccharide fractions. They, may be obtained from a water extract after a preceded hexane, dichlormethane and methanol soxhlet extraction. The organic solvent extract is discarded. The water extraction may be carried out for 1 hour at 80° C. After cooling to room temperature, 1 g $NaN_3$ may be added. The solution may be centrifuged for 30 min at 8000 Upm and washed twice with distilled water. The solution may be dialysed at 4° C. in a VIKING dialysis tubing 36/32, diameter 27 mm for 96 hours with 12 times water exchange. The dialysed water fraction may be centrifuged and freeze-dried. The term LAT543 relates to a precipitate obtainable from 3 g of the brownish residue of the hot water dissolved in 300 ml distilled water and adding under stirring at 4° C. 300 ml ethanol (1:1 water: ethanol) drop by drop. The precipitation may be centrifuged, dissolved in a small amount of distilled water and freeze-dried whereas the term $LAT_{543}$-0 relates to a precipitate obtainable from the supernatans of LAT-543 precipitation treated in the same way as said above with 900 ml ethanol (1:4 water:ethanol) to get the polysaccharide precipitation of LAT543-0. Precipitates of both LAT543 and LAT543-0 may be freeze-dried and dissolved in water in varies concentrations for testing.

| Yield | g | g |
|---|---|---|
| Non dialyzable hot water extract | 16.7 | 3.34 |
| 1:1 ethanol precipitation | 2.01 | 0.40 |
| 1:4 ethanol precipitation | 0.04 | 0.01 |
| Total amount of polysaccharides | 2.05 | 0.41 |

The sugar content of LAT543 and LAT543-0 may be quantified according to BLAKENEY et. al. (1983). The uronic acid content of LAT543 and LAT543-0 may be quantified according to BLUMENKRANZ and ASBOE-HANSEN (1973). The nitrogen content as albumine of LAT543 and LAT543-0 may be quantified according to LOWRY (1951).

The term "M-W-EL1299" relates to an extract obtainable from *Mucuna pruriens* by shaking 200 g pulverised seed material of *Mucana pruriens*, preferably at room temperature, in 200 ml n-hexane, preferably for 18 hours. After filtration, the material may be washed with 100 ml n-hexane and filtered. The filtrates may be collected and the solvent distilled off to obtain a yellowish oil. The residue of the n-hexane extraction is subsequently shaken, preferably for 18 hours, at room temperature, in acetone (200 ml), preferably followed by a step of filtration. The residue may be extracted one or more times with 200 ml acetone by further shaking, preferably for 18 hours, followed by a step of filtration. Subsequently, the residue may be washed with acetone (100 ml) and filtered. After pooling, the filtrates may be evaporated by distillation, preferably under reduced pressure, yielding a yellowish mass. The residue (obtained from the above extractions, ca. 96 g) is shaken, preferably for 18 hours at room temperature, in 500 ml of a mixture of water-EtOH, 1:1 with 0.5% ascorbic acid. The solvent may be filtered and concentrated, preferably under reduced pressure at a temperature of 35° C. The extraction procedure may repeated one, two, three, four or more times. After concentration, the filtrates may be collected and the solvent removed under vacuum to get a solid mass. Of course, larger or smaller quantities of M-W-EL1299 can be prepared, simply by reducing or increasing the amount of seeds and solvent.

The term "M-W0100" relates to an extract obtainable from *Mucuna pruriens* by shaking the M-EL0100 extract (vide supra), preferably for 18 hours at room temperature in demineralized water, followed by a step of filtration. The extraction may be repeated one, two, three, four or more times. Subsequently, the filtrates may be pooled together and water distilled off, after passing $SO_2$ to prevent the oxidation of L-DOPA. Of course, larger or smaller quantities of M-W0100 can be prepared, simply by reducing or increasing the amount of input material (M-EL0100 fraction) and solvent.

The term "MWEL0700" relates to an extract obtainable from *Mucuna pruriens* by extracting *Mucuna pruriens* with a 1:1 mixture of water:ethanol, preferably without ascorbic acid addition, by shaking 100 g powder with 500 ml of this solvent mixture, preferably for 18 hrs at room temperature. The solvent may be evaporated at reduced temperature to dryness. Of course, larger or smaller quantities of "MWEL0700" can be prepared, simply by reducing or increasing the amount of *Mucuna pruriens* powder and solvent.

The term "M-ML0100" relates to an extract obtainable from *Mucuna pruriens* by shaking 10 g of pulverized steeds of *M. pruriens*, preferably for 18 hours at room temperature, in methanol (50 ml), followed by a step of filtration. The extraction of the residue is followed by two or more steps of extraction with methanol followed by a filtration step. The filtrates may be pooled together and the solvent distilled off to yield a semi-solid mass. Of course, larger or smaller quantities of "M-ML0100" can be prepared, simply by reducing or increasing the amount of *Mucuna pruriens* powder and solvent.

In certain cases it may be preferable to reduce or increase the incubation time with the solvent. Accordingly, the incubation time may be less than 18 hours, i.e. 17, 16, 15, 14, 13, 12, 11, 10 hours or more than 18 hours, i.e. 19, 20, 21, 22, 23 or 24 hours. When performing the extraction under pressure, substantially less time may be sufficient to prepare the extract. Preferably, the extraction is performed at room temperature, however, in certain cases it may be preferable to reduce or increase the temperature in order to improve the amount or quality of the extract. Accordingly, also preferred are temperatures such as about 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C. or 40° C., wherein these temperatures may vary by ±0.5° C.

The present invention also relates to the use of *Mucuna pruriens* seeds or of one or more components, substances, fractions or mixtures of substances obtained or extracted from *Mucuna pruriens* for the preparation of a pharmaceutical composition (a) for inhibiting L-Dopa and/or dopamine metabolism; (b) for improved L-Dopa absorption, resulting in an earlier onset of L-Dopa efficacy; and (c) for a longer duration of L-Dopa efficacy.

Moreover, the present invention also provides the use of *Mucuna pruriens* seeds or one or more components, fractions or mixtures of substances obtained or extracted from *Mucuna pruriens* for the preparation of a pharmaceutical composition for neuroprotection or neurostimulation.

The term "neuroprotection" means protection of nerve tissues. Furthermore, neuroprotection is the protection of nerve cells and their function against endogene or exogene physical or chemical factors negatively influencing the metabolism, survival or function of nerve cells such as for example heat application, Roentgen radiation, ischaemia, neurotoxins, oxidants, intoxications including heavy metals, infections and sequelae of vaccinations, systemic metabolic diseases and disturbances in endocrine or electrolyte homeostasis.

The term "neurostimulation" means stimulation of nerve tissues. Moreover, neurostimulation is the improvement, enhancement or restoration of function of nerve cell tissues, both centrally and peripherally, through stimulation of cellular growth or nerve cell activity, both with respect to signal conduction and transduction, by physical means such as for example electro-stimulation or chemical-pharmacological means. The neuroprotective effect of *Mucuna pruriens* is registered by in vitro measurements of the survival and growth rate of mesencephalic or motor-neurons after pretreatment with *Mucuna* extract and exposure to a damaging (oxidative, toxic) stress agents.

The present invention also provides the use of one or more *Mucuna pruriens* components, fractions or mixtures of substances obtained or extracted from *Mucuna pruriens* for the preparation of a pharmaceutical composition for preventing, alleviating or treating neurological diseases. The term "neurological disease" includes diseases such as Parkinson disease (PD), Alzheimer's disease (AD), amyotrophic lateral sclerosis (aALS), motoneuron disease.

A preferred embodiment of the invention the use relates to neurological degenerative diseases and comprises a large number of diseases known to the person skilled in the art. According to the present invention, neurodegenerative or neurological degenerative diseases fall into one of the following groups A to D:

A: Degenerative and Heredodegenerative Diseases (nerve tissue atrophy is primair). This group includes, but is not limited to: Parkinson's disease, Chorea Huntington, Hallervorder-Spatz disease, Alzheimer's disease, senile dementia, Creutzfeldt-Jakob disease, artheriosclerotic dementia, cerebral thrombangitis obliterans.

B: Metabolic and nutritional Disorders (secondair to systemic disorder). This group includes, but is not limited to: disturbances in lipoid metabolism (a.o. Gaucher, Niemann-Pick, Tay-Sachs, Hurler, Refsum), Leukodystrophien, disturbances in aminoacid, carbohydrate metabolism, hepatolenticular degeneration, etc. deficiencies such as Vitamin B12 deficiency or folic acid deficiency.

C: Systemic diseases, endocrine disturbances and autoimmune reactions afflicting the nervous system: This group includes, but is not limited to: hypothyreose, hypo- and hyperparathyreoidismus, Collageen diseases, systemic lupus erythematodes, sarcoidosis, leukoencephalopathy, demyelisation.

D: Nervous tissue damage by various endogenic and exogenic factors: This group includes, but is not limited to: ischemiam, trauma's, physical noxen, intoxications with metals (mercury, lead, aluminum, etc) and neurotoxins, alcohol abuse, sequelae of infection and vaccination.

Neurological degenerative diseases, as used herein, that may be prevented, treated or alleviated are diseases characterized by the formation of nervous system lesions. These lesions include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, or syphilis; (5) degenerative lesions, in which a portion of the nervous system is destroyed or injured as a result of a degenerative process including but not limited to, degeneration associated with Parkinson's disease, Alzheimer's disease, Huntington's chorea, or amyotrophic lateral sclerosis (ALS); (6) lesions associated with nutritional diseases or disorders, in which a portion of the nervous system is destroyed or injured by a nutritional disorder or disorder of metabolism including, but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis. Neurological degenerative disease associated with the formation of lesions and/or behavioral disorders include, but are not limited to, Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception.

In a more preferred embodiment the neurological degenerative disease is selected from the group of degenerative and heredodegenerative diseases including Parkinson's disease, Chorea Huntington, Hallervorder-Spatz disease, Alzheimer's disease, senile dementia, Creutzfeldt-Jakob disease, artheriosclerotic dementia, cerebral thrombangitis obliterans or other diseases, according to any one of the diseases mentioned under group A to D of neurodegenerative diseases, which can be caused by exogenic or endogenic factors. The term "endogenic factor" means originating from within an organism, the term "exogenic factor" means originating from outside the organism.

Yet another more preferred embodiment relates to a neurological degenerative disease which is Parkinson's disease. In a particularly preferred embodiment of the present invention, Parkinson's disease is treated by preventing acute or chronic L-Dopa toxicity. As the present invention discloses that in patients treated with *Mucuna pruriens* much higher levels of L-Dopa are tolerated without the induction of toxic side-effects, *Mucuna pruriens* and its extracts may be used for suppressing toxic side effects. Particularly preferred are those fractions or extracts of *Mucuna pruriens* which show neuroprotective or neurostimulatory activity.

Still another preferred embodiment relates to the use of *Mucuna pruriens* seed powder or one or more *Mucuna pruriens* components, fractions or mixtures of substances obtained or extracted from *Mucuna pruriens* for the preparation of a pharmaceutical composition for preventing, alleviating or treating a neurological degenerative disease, wherein said components, fractions or mixtures of substances obtained or extracted from *Mucuna pruriens* can be or contain any chemical entity contained in *Mucuna pruriens*. However, preferably said components, fractions or mixtures of substances are selected from the group consisting of alkaloids, proteins, peptides, polysaccharides, glycosides, glycoproteins, sterols, phytochemicals like 1-methyl-3-carboxy-6,7-dihydroxy-1,2,3,4-tetrahydroisoquinolone, 5-hydroxytryptamine, 5-methoxy-n,n-dimethyltryptamine-n-oxide, 5-oxyindole-3-alkylamine, 6methoxyharman, Alanine, Arachidic-acid, Arginine, Aspartic-acid, Behenic-acid, Beta-carboline, Beta-sitosterol, Bufotenine, Choline, Cis-12,13-epoxyoctadec-trans-9-cis-acid, Cis-12,13-epoxyoctadec-trans-9-enoic-acid, Cystine, DOPA, Gallic-acid, Glutamic-acid, Glutathione, Glycine, Histidine, L-DOPA, Lecithin, Leucine, Linoleic-acid, Mucunadine, Mucunain, Mucunine, Myristic-acid, N,n-dimethyltryptamine, N,n-dimethyltryptamine-n-oxide, Nicotine, Oleic-acid, Palmitic-acid, Palmitoleic-acid, Phenylalanine, Phosphorus, Proline, Protein, Prurienidine, Prurienine, Saponins, Serine, Serotonin, Stearic-acid, Threonine, Tryptamine, Tyrosine, Valine, Vernolic-acid or phosphatides such as phosphatidylcholin, phosphatidylethanolamine, phosphatidylserin, phosphatidylinositol. Preferred alkaloids include L-3-Carboxy-6,7-dhihydroxy-1,2,3,4-tetrahydroisoquinoline, L-3-Carboxy 7,8-dhihydroxy-1,1-dimethyl, 1,2,3,4tetra-hydroisoquinoline, L-3-Carboxy-6,7-dihydroxy-1,1-dimethyl1,2,3,4-tetrahydroisoquinoline, L3-Carboxy-6,7-dihydroxy-1 β-methyl-1,2,3,4-tetraisoquinoline and 1-methy-3-carbox-6,7-dihydroxy-1,2,3,4-tetrahydroisoquinoline. More preferably said components, fractions or mixtures of substances contain L-Dopa and one or more components contained in *Mucuna pruriens*. Another preferred embodiment of the invention relates the use of components, substances, fractions or mixtures of substances isolated form *Mucuna pruriens* which do not contain a pharmaceutically effective amount or only traces of L-Dopa.

Another preferred embodiment of the invention relates to the use of alcohols and/or mixtures thereof, used for the extraction of *Mucuna pruriens* components, fractions or mixtures of substances, wherein the alcohol is selected from the group consisting of hexanol, ethanol, methanol, isopropanol, n-butanol and propanol.

A further preferred embodiment relates to the use of organic solvents and/or mixtures thereof, used for the extraction of *Mucuna pruriens* components, fractions or mixtures of substances, wherein the organic solvent is selected from the group consisting of chloroform, $CO_2$, hypercritical $CO_2$, ether, DMSO, hexane, ethylacetate, dichlormethane and acetone.

Yet another preferred embodiment relates to the use of polar solvents and/or mixtures thereof, used for the extraction of *Mucuna pruriens* components, fractions or mixtures of substances, wherein the polar solvent is selected from the group consisting of water, ethanol, methanol, propanol and isopropanol.

A more preferred embodiment relates to the use of a 1:1 mixture of water and ethanol containing 0.5% ascorbic acid [% w/w]. Preferably this step is preceded by an initial extraction step with n-hexane followed by an extraction step with acetone.

However, the invention also relates to the use of mixtures, wherein the ethanol concentration is preferably between 10% and 75%, more preferred between 20% and 65%, even more preferred between 30% and 60% and most preferred 50%. Preferably said mixture contains between 0.01% and 2% ascorbic acid, more preferred between 0.1% and 1.2%, even more preferred between 0.3% and 0.9% and most preferred 0.5% ascorbic acid. However, in some cases it may be advantageous to add no ascorbic acid to the extraction solution.

Another preferred embodiment relates to the use of one or more solvents or mixtures of the solvents for the extraction process. According to this embodiment, two or more solvents selected from the group of alcohols, organic solvents and polar solvents are used for the extraction process.

Still another embodiment relates to fractionated extraction.

In a preferred embodiment of the present invention's use, the extract of *Mucuna pruriens* is (a) a neurostimulatory extract of *Mucuna pruriens* selected from the group consisting of M-PL0100, M-EL100, M-BL0100 and LAT543-0 or (b) a neuroprotective extract of *Mucuna pruriens* selected from the group consisting of M-W-EL1299, M-W0100, MWEL0700 and M-ML0100. One or more of the extracts may be combined in the same pharmaceutical composition.

In another preferred embodiment, the present invention's pharmaceutical composition comprises (a) a neurostimulatory extract of *Mucuna pruriens* selected from the group consisting of M-PL0100, M-EL100,M-BL0100 and LAT543-0 or (b), a neuroprotective extract of *Mucuna pruriens* selected from the group consisting of M-W-EL1299, M-W0100, MWEL0700 and M-ML0100. One or more of the extracts may be combined in the same pharmaceutical composition.

The present invention also provides a method of preparing extracts or extract-fractions of *Mucuna pruriens* comprising (a) extracting seeds of *Mucuna pruriens* with n-hexane to provide a first extract solution; (b) filtering the first extract solution; (c) extracting the filter retentate of (b) with acetone to provide a second extract solution; (d) filtering the second extract solution; (e) extracting the filter retentate of (d) with a 1:1 mixture of water and ethanol containing 0.5% ascorbic acid to provide third extract solution; (f) filtering the third extract solution; (g) repeating at least four times the extraction procedure of (e) with the retentate obtained by (f); and (h) concentrating the pooled extract solutions. However, the invention also relates to methods comprising additional filtration, washing or extraction steps. The term "filtration" means filtration by passing through a filter. The term "washing" means to wash the filtered residue on a filter with the mentioned solvent. The term "concentrating" means evaporation at low temperature (40-75° C.) and at normal or under reduced pressure. Water extract could alternatively be freeze-dried.

Furthermore, the invention also relates to a method wherein hexane in the initial step and/or acetone in the second extraction step is replaced by at least one other organic solvent as defined above. Furthermore, the invention also relates to a method wherein the ethanol content and/or the content of ascorbic acid are modified. In particular, the ethanol concentration may be modified to any concentration between 10% and 75%, more preferred between 20% and 65%, even more preferred between 30% and 60% and most preferred between 45% and 55%. Preferably said mixture contains between 0.01% and 2% ascorbic acid, more preferred between 0.1% and 1.2%, even more preferred between 0.3% and 0.9% and most preferred between 0.45% and 5.5% ascorbic acid. However, in some cases it may be advantageous to add no ascorbic acid to the extraction solution. Furthermore, this method of the invention allows replacement of ethanol with other alcoholic compounds selected from the group consisting of propanol, isopropanol and methanol. The method for preparing extracts or extract-fractions of *Mucuna pruriens* comprises repeating the extraction procedure of step (e) on the retenate of step (f). Nevertheless, in some cases it may be advantageous to eliminate this step from the method or to repeat this step at least once, at least twice, at least three times, at least four times, at least five times or up to ten times.

The present invention also provides a method of preparing extracts or extract-fractions of *Mucuna pruriens* comprising (a) extracting seeds of *Mucuna pruriens* with an alcohol, wherein the alcohol is (i) methanol, ethanol and/or propanol to provide a first extract solution; (b) filtering the first extract solution; (c) repeating at least two times the extraction procedure of (a) with the retentate obtained by (b); and concentrating the pooled extract solutions. Preferably the first extract solution consists of 10-100% alcohol, more preferably of 30-100% alcohol, even more preferably of 70-100% alcohol, still more preferably of 90-100% alcohol and most preferably of 99-100% alcohol. This method for preparing extracts or extract-fractions of *Mucuna pruriens* comprises repeating the extraction procedure of step (a) with the retenate of step (b). In some cases it may be advantageous to eliminate this step from the method or to repeat this step at least once, at least twice, at least three times, at least four times, at least five times or up to ten times. Furthermore, in some cases it may be advantageous to add organic solvents such as e.g. Dimethyl Sulfoxide (DMSO) or water.

In a preferred embodiment the method further comprises solubilizihng said extract or extract-fractions of *Mucuna pruriens* in a solvent comprising DMSO and/or distilled water. Resolubilization may be supported by heat treatment of the extract in the presence of the solubilizing agent, appropriate conditions can easily established by the person skilled in the art.

The invention also relates to a method for the preparation of extracts of extract fractions of *Mucuna pruriens,* comprising extracting the seed of *Mucuna pruriens* with $CO_2$ or mixtures from $CO_2$ and butane, propane or other gases under supercritical conditions or different pressures and temperatures, to obtain purification and selection of substances or fractionation of *Mucuna pruriens* extracts.

The present invention also provides the use of *Mucuna pruriens* seeds or seed powder, as well as extracts or extract fractions of *Mucuna pruriens,* obtainable by the methods of the invention, for the preparation of a pharmaceutical composition for treating neuronal diseases. The term "obtainable" or "obtained" means produced, isolated or extracted by any of the methods of the invention.

A preferred embodiment of the invention relates to the use of extracts or extract-fractions or of extracted components, substances or mixtures of substances wherein *Mucuna pruriens* is used in comminuted form, as granules, powder, precipitate, fraction, extract, dried extract and/or exudates, preferably as extract.

Another preferred embodiment of the invention relates to the use of *Mucuna pruriens* seeds or seed powder or extracts of *Mucuna pruriens* or extract-fractions or of extracted components, substances or mixtures of substances, wherein said *Mucuna pruriens* components, substances, fractions or mixtures of substances obtained therefrom are used in combination with one or more other active agents. The term "active agent" as used herein relates to therapeutic agents or products clinically used or to be used in future, such as components contained in amino acid fractions with or without L-DOPA, isoquinoline alcaloid fractions, polysaccharide or glycoprotein fractions, phosphatides, fatty acid fractions for the treatment of neurological diseases in which a combination of *Mucuna pruriens* components, substances, fractions or mixtures of substances with the active agent could be of clinical benefit.

*Mucuna pruriens* components, substances, fractions or mixtures of substances will be formulated and dosed in a fashion consistent with good medical practice, taking into account the clinical condition of the individual patient (especially the side effects of treatment with said *Mucuna pruriens* extract alone), the site of delivery, the method of administration, the scheduling of administration, and other factors known to practitioners. The "effective amount" for purposes herein is thus determined by such considerations.

Pharmaceutical compositions containing the extracts of the invention are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The extract is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman et al., *Biopolymers,* 22:547-556 (1983)), poly (2-hydroxyethyl methacrylate) (Langer et al., *J. Biomed. Mater. Res.* 15:167-277 (1981), and Langer, *Chem. Tech.,* 12:98-105, (1982)), ethylene vinyl acetate (R. Langer et al.) or poly-D-(–)-3-hydroxybutyric acid (EP 133,988). Sustained-release compositions also include liposomally entrapped extracts. Liposomes containing the *Mucuna pruriens* extract are prepared by methods known by the person skilled in the art. Ordinarily, the liposomes are of the small (about 200-800 Angstroms) unilamellar type in which the lipid content is greater than about 30 mol. percent cholesterol, the selected proportion being adjusted for the optimal therapy.

For parenteral administration, in one embodiment, the extract is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example., the formulation preferably does not include oxidizing agents and other compounds that are known to be deleterious to the therapeutical effectiveness of *Mucuna pruriens* extracts. Generally, the formulations are prepared by contacting the *Mucuna pruriens* extract uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate may also be useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The *Mucuna pruriens* extract is typically formulated in such vehicles at a concentration of about 0.1 mg/ml to 100 mg/ml, preferably 1-10 mg/ml, at a pH of about 3 to 8.

Any *Mucuna pruriens* extract to be used for therapeutic administration can be sterile. Sterility is readily accomplished by filtration through sterile filtration membranes (e.g., 0.2 micron membranes). Therapeutic *Mucuna pruriens* compositions generally are placed into a container having a sterile access port, for example, an intravenous solution bag or vial having a stopper pierceable by a hypodermic injection needle.

*Mucuna pruriens* ordinarily will be stored in unit or multi-dose containers, for example, sealed ampoules or vials, as an aqueous solution or as a lyophilized formulation for reconstitution. The infusion solution is prepared by reconstituting the lyophilized *Mucuna pruriens* extract using bacteriostatic Water-for-Injection.

Another preferred embodiment of the invention relates to the use of extracts or extract-fractions or of extracted components, substances or mixtures of substances wherein the *Mucuna pruriens* components, substances, fractions or mixtures of substances are formulated as infusion solution, injection solution, for oral forms of application, as a therapeutic pack, a granulate, a food supplement or in form of clysters.

Yet another preferred embodiment of the invention relates to the use of extracts or extract-fractions or of extracted components, substances or mixtures of substances in oral, topical and/or parenteral applications.

The invention also provides a pharmaceutical pack or kit comprising one or more containers filled with *Mucuna pruriens* components, substances, fractions or mixtures of substances or the pharmaceutical compositions of the invention. Associated with such container(s) can be a notice in the form prescribed by a national health authority regulating the manufacture, use or sale of pharmaceuticals or biological products, which notice reflects approval by the agency of manufacture, use or sale for human administration. In addition, the *Mucuna pruriens* extracts of the present invention may be employed in conjunction with other therapeutic compounds.

The invention also relates to a method of treatment of an individual in need of a neuroprotective or neurostimulatory activity comprising administering to such an individual a pharmaceutical composition comprising an amount of *Mucuna pruriens* seeds or of one or more components, substances, fractions or mixtures of substances obtained or extracted from *Mucuna pruriens* which is effective in providing the required neuroprotective or neurostimulatory activity in such an individual. For example, a Parkinson disease patient treated with L-Dopa typically develops acute toxic side effects and side effects following long term use such as such as dyskinesia. By administering to an individual a pharmaceutical composition comprising *Mucuna pruriens* seeds or an extract thereof, said toxic side effects are less severe, absent or are deferred. The pharmaceutical composition containing *Mucuna pruriens* components may be administered as a formulation of whole seed powder, an extract thereof, or may be administtered as extract fractions in combination with L-Dopa or separately.

The present invention also relates to a method of treatment of an individual in need of a wider therapeutic window in L-Dopa therapy and to prevent an early need for combination therapy with, for example, a decarboxylase inhibitor, a decarboxylase, COMT, or MAO inhibitor, or other anti-Parkinson drugs such as for example amantadine, pergolide, ropinirole, cabergoline, pramipexole, said method comprising administering to such an individual a pharmaceutical composition comprising an amount of *Mucuna pruriens* seeds or of one or more components, substances, fractions or mixtures of substances obtained or extracted from *Mucuna pruriens* which is effective in providing the required wider therapeutic window in such an individual. A wider therapeutic window may allow to treat patients much longer with L-Dopa and with higher L-Dopa doses without the need for combination therapy and the resulting negative side-effects thereof.

The present invention also relates to a method of treatment of an individual, preferably a Parkinson's disease patient, in need of a pharmaceutical composition capable of suppressing the toxic acute and/or chronic side effects of L-Dopa, said method comprising administering to such an individual a pharmaceutical composition comprising an amount of *Mucuna pruriens* seeds or of one or more components, substances, fractions or mixtures of substances obtained or extracted from *Mucuna pruriens* which is effective in suppressing the toxic acute and/or chronic side effects of L-Dopa in such an individual.

The present invention also relates to a method of treatment of an individual, preferably a Parkinson's disease patient, in need of an early onset of L-Dopa activity, said method comprising administering to such an individual a pharmaceutical composition comprising an amount of *Mucuna pruriens* seeds or of one or more components, substances, fractions or mixtures of substances obtained or extracted from *Mucuna pruriens* which is effective in providing an early onset of L-Dopa activity in such an individual. Said extract of *Mucuna pruriens* may be the source of L-Dopa, however, exogenous L-Dopa may be added to the pharmaceutical composition. This method is based on the surprising clinical observation that patients treated with *Mucuna pruriens* show an increased absorption of L-Dopa and early onset of L-Dopa activity.

Moreover, the present invention also relates to a method of treatment of an individual, preferably a Parkinson's disease patient, in need of sustained L-Dopa plasma levels without a need for combination therapy to inhibit peripheral L-Dopa conversion, said method comprising administering to such an individual a pharmaceutical composition comprising an amount of *Mucuna pruriens* seeds or of one or more components, substances, fractions or mixtures of substances obtained or extracted from *Mucuna pruriens* which is effective in providing the sustained L-Dopa plasma level in such an individual.

Finally, the present invention relates to a method of treatment of an individual, preferably a Parkinson's disease patient, in need of an inhibition of L-Dopa and/or dopamine metabolism, said method-comprising administering to such an individual a pharmaceutical composition comprising an amount of *Mucuna pruriens* seeds or of one or more components, substances, fractions or mixtures of substances obtained or extracted from *Mucuna pruriens* which is effective inhibiting L-Dopa and/or dopamine metabolism in such an individual.

Typically, 5 g to 60 g *Mucuna pruriens* or an extract thereof are administered to a patient. However, the amount particularly depends on factors such as the body weight, age or disease condition. Therefore, at least 5 g, at least 10 g, at least 15 g, at least 20 g, at least 25 g, at least 30 g, at least 35 g, at least 40 g, at least 45 g, at least 50 g, at least 55 g or at least 60 g of *Mucuna pruriens* may be appropriate for achieving the desired therapeutical effect. As the active components may be concentrated in a particular extract, smaller quantities may already be sufficient to induce the desired effect in the patient.

The figures show:

FIG. 1: Interpatient means of the plasma levels of L-Dopa following LD/DC 200/50, 15 g and 30 g *Mucuna pruriens*. The horizontal axis shows time in hrs:min, the vertical axis the L-Dopa plasma levels in ng/ml.

FIG. 2: The intrapatient means of the plasma levels of L-Dopa following LD/DC 200/50, 15 g and 30 g *Mucuna pruriens*. The difference in plasma levels is presented in percentage difference in L-Dopa plasma level compared with the plasma level following LD/DC (=100%).

Figure 3:
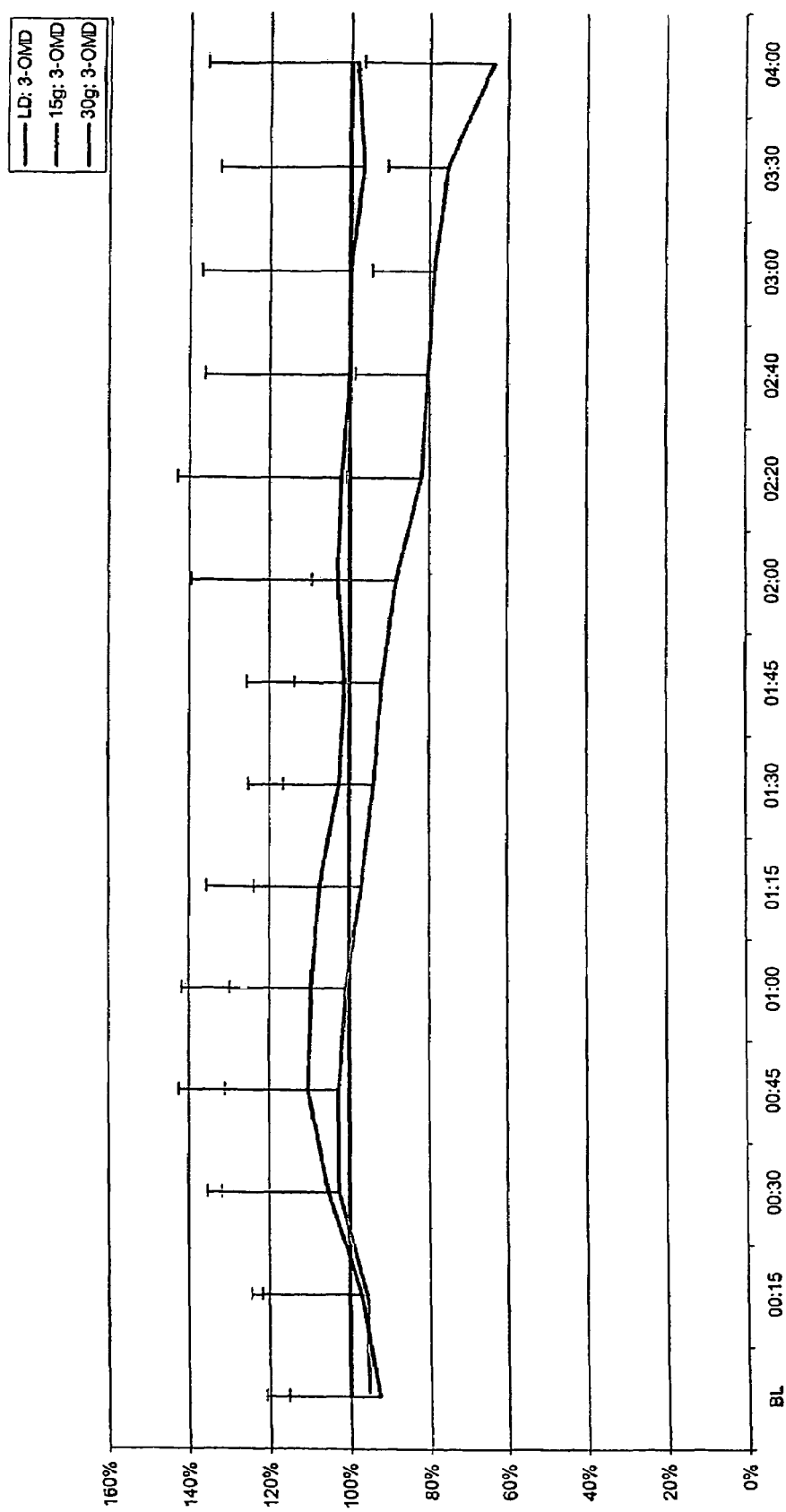

FIG. 3: The intrapatient means of the plasma levels of 3-O-Methyl-Dopa (3-OMD) following LD/DC 200/50, 15 g and 30 g *Mucuna pruriens*. The difference in plasma levels is presented in percentage difference in 3-OMD plasma level compared with the plasma level following LD/DC (=100%).

The invention is illustrated by the following examples:

CLINICAL STUDIES

EXAMPLE 1

Patients, Methods and Study Design

Patient Selection:

Patients with idiopathic PD fulfilling the Queen Square Brain Bank criteria (9) with motor fluctuations and a defined short duration L-Dopa response (1.5-4 hours) were eligible for inclusion. Clinically relevant peak dose dyskinesias following each morning dose of their current medication were a further pre-requisite. Patients were also required to have been stable on a fixed dose of treatment for a period of at least one month prior to starting the study.

Patients were excluded if their current drug regime included slow-release formulations of L-Dopa, COMT inhibitors, selegiline, anticholinergic drugs, or other drugs that could potentially interfere with gastric absorption (e.g. antacids). Other exclusion criteria included patients with psychotic symptoms or those on antipsychotic treatment patients with clinically relevant cognitive impairment, defined as MMS (Mini Mental State) score of less than 24 (10), risk of pregnancy, Hoehn & Yahr stage 5 in "off"-status, severe, unstable diabetes mellitus, and medical conditions such as unstable cardiovascular disease or moderate to severe renal or hepatic impairment. Full blood count, liver and renal function blood tests were taken at baseline and after completion of the study.

Study Design:

The trial was randomized, double-blind and cross-over in design. Each patient was randomized to the order in which either LD/DC or one of the two dosages of *Mucuna pruriens* seed powder preparation were administered in a single-dose challenge in double-dummy fashion in three consecutive sessions. Randomization was by computer generation of a treatment number, allocated to each patient according to the order of entry into the study. Study drugs were kept at the pharmacy of the National Hospital for Neurology and Neurosurgery, London, and dispensed by an independent pharmacist. The Medicines Control Agency/Department of Health, UK, issued an exemption from licenses order for the study drug. The study was approved by the Joint Ethics Committee of University College London/University College London Hospitals. All patients gave informed consent.

Study Drug:

The *Mucuna pruriens* seed powder preparation was a light, yellowish powder, which was manufactured and formulated under Good Manufacturing Practice (GMP) conditions in Germany (Wiewelhove GmbH TM) from raw bean material obtained in India and packed in sachets (unit) of 7.5 grams. To enhance stability and dissolvability in water, and to improve taste ascorbic acid, tangerine oil, silicium dioxide, saccharine-Na and citric acid, as well as sorbitol and lecithin were added. Matching placebo sachets containing powder material with the same consistency, colour and taste were produced for the study. Quality Assurance Certificates for the preparation and placebo were obtained from an independent laboratory (LAT GmbH, Munich, Germany). The HPLC-analysis provided demonstrated a L-Dopa content of 4.86% or 250 mg per sachet.

Single Dose Challenges:

Patients were admitted to the hospital for an overnight stay prior to the challenging session the next morning on three separate occasions at weekly intervals. After withdrawal of all antiparkinsonian medication from midnight the previous day challenges were performed at exactly the same time in the morning in each patient under fasting conditions with the exception of black tea or coffee and water.

Patients were randomized to the order of the days on which they received: 200 mg L-Dopa/50 mg carbidopa as capsule formulation plus 4 sachets of 7.5 gr placebo powder formulation, or either: 15 g=2 sachets of *Mucuna* seed powder (containing 500 mg L-Dopa) plus two sachets of placebo powder plus a placebo capsule identical in shape, colour and taste to the LD/DC capsule, or 30 g=4 sachets of *Mucuna* seed powder (containing 1000 mg L-Dopa) plus a placebo capsule.

Pharmacokinetic Assessment:

Prior to the challenge a 22 G intravenous catheter was inserted in the patients forearm. Blood samples of 5 ml each were taken at baseline and 15, 30, 45, 60, 75, 90, 105, 120, 140, 160, 180, 210 and 240 minutes after intake of the medication or until a full "off-state" had been reached if this occurred earlier than 240 minutes after drug ingestion. Samples were centrifuged immediately at the end of each assessment and stored deep frozen until assayed. Plasma L-Dopa and 3-O-methyl-dopa levels were assessed by high pressure liquid chromatography (HPLC).

On the last assessment additional blood was drawn for routine hematology, blood sugar, liver and renal function.

Clinical Assessment:

Motor function was assessed using UPDRS (United Parkinson's Disease Rating Scale) motor score and "BrainTest" (11): a tapping test performed with the patient's more affected hand on the keyboard of a laptop computer. These tests were carried out at baseline and then immediately following each blood sample until patients had reached their full "on"-stage. Thereafter at 3 intervals of 20 minutes, and 30 minutes intervals until 240 minutes after drug administration, or until patients had reached their baseline "off"-status, whichever came first. Once patients had reached their full "on"-state, video recordings were performed three times at 20 minutes intervals. As certain mental and motor tasks have been shown to increase dyskinesia (12), the following tasks were chosen to be carded out during each video session:

1. Sitting still for 1 minute
2. Performing mental calculations
3. Putting on and buttoning a coat.
4. Picking up and drinking from a cup of water
5. Walking Videotapes were rated independently by two blinded raters using modified versions of the Goetz Rating Scale and the Abnormal Involuntary Movements Scale (AIMS) to document a possible increase in drug induced dyskinesia.

Modified versions were applied in that global rating and facial muscles were excluded for AIMS, while for Goetz phenomenological rating was excluded and only choreatic movements were counted.

The actual occurrence and severity of dyskinesia was measured with a Dyskinesia Monitor, a small ambulatory electronic device developed to objectively assess dyskinesias over prolonged periods of time (13). The device is taped to the patients shoulder on their more affected side. The monitor records during the entire time of the challenging session and provides an absolute value being the result of the frequency and severity of occurring dyskinesias.

Blinding:

Randomization information was kept in a blinded format with the company that had manufactured and supplied the active drugs and the matching placebos. Emergency envelopes with the randomization code were also kept with the head pharmacist at the National Hospital for Neurology and Neurosurgery, London. Blinding was maintained until after the database was locked.

Statistics and Data Analysis:

The double-blind trial was powered to detect a difference of 25% between AIMS scores on treatment, which was considered a clinically relevant change based on previous publications (13) and on clinical judgment. Power calculation showed that eight patients completing the treatment arms were required to obtain a power of 80% at the 5% significance level. All data sets were assessed and means/medians were compared using Wilcoxon's non-parametric signed rank-test or paired-samples t-test, as appropriate. Both inter- and intra-patient data have been analyzed. The two video raters' AIM and Goetz scores were combined for analysis. Interrater reliability was assessed using kappa analysis, weighted according to how close agreement between the raters was (Stata Statistical Software Release 6.0).

Patient Population:

Nine patients (five women and four men) were enrolled in the study. One patient dropped out due to transient vomiting during ingestion of the first study medication (30 g *Mucuna*).

Since absorption was not likely to have taken place in this patient, this patient was excluded from further evaluation. Eight patients completed the three sessions of this study. Patients mean age was 62.2 years (range 50-72). Mean disease duration was 12.4 years (range 7-17). Mean Hoehn & Yahr stage (in "off"-stage) was 3.5 (range 2.5-4). Patients took a mean daily L-Dopa dose of 572 mg prior to the trial. Other antiparkinsonian medication taken by any patient were amantadine in two (200 mg), pergolide in three (mean, 3.2 mg), and ropinirole (18 mg), cabergoline (6 mg) and pramipexole (1.4 mg) in one patient each.

EXAMPLE 2

Pharmacokinetic Results

In FIG. 1 the mean serum L-Dopa levels are presented. The mean $C_{max}$ for both 15 g and 30 g were significantly higher than for LC/DC (+57% and +163%, respectively). $T_{max}$ was reached for 15 g *Mucuna* after 30 minutes, for 30 g *Mucuna* after 45 minutes and for LD/DC after 90 minutes. There were no significant differences in $T_{1/2}$ among the three study drugs. The mean L-Dopa plasma levels of 15 g *Mucuna* started to decline below the level of LD/DC after approximately 80 minutes. In view of interpatient variability and corresponding standard deviations (at $C_{max}$ LD; 1600 ng/ml, 15 g: 5962 ng/ml, 30 g: 7213 ng/ml) the intrapatient means are presented in FIG. 2 the differences between he study drugs expressed as percentage difference from LD/DC (LD/DC=100%). The peak difference for both 15 g and 30 g *Mucuna* is reached after 15 minutes (+1659% and +3155%, respectively).

Also on the basis of intrapatient means the L-Dopa plasma level of 15 g *Mucuna* declines under the level of LD/DC after 90 minutes, whilst 30 g *Mucuna* maintains a difference of +88% to +113%. The means of cumulative intrapatient plasma relations (intrapatient AUC differences, AUC LD/DC=100%) demonstrate a difference of +31% for 15 g and +159% for 30 g *Mucuna*. Although values tended to be higher in patients administered LD/DC, 3-OMD AUC values were not significantly different between the three study regimens. The intrapatient means for 3-OMD (FIG. 3) did also not show a difference in the plasma levels for LD/DC and 30 g *Mucuna*, but for 15 g *Mucuna* a steady decline below the levels of LD/DC was notable, which reached a difference of −36% after 240 minutes. This difference was significant (p=0.009 at 240 minutes).

EXAMPLE 3

Results of the Clinical Assessment

Results and statistical significance of differences are shown in table 1 and 2. Time to full "on" status was 23 minutes (33.4%) shorter on 15 g *Mucuna* than on LD/DC, and 34 minutes (49.5%) shorter on 30 g *Mucuna*. Time to beginning of switching on was reduced by 27 minutes (49%) on 15 g and by 32 minutes (58%) on 30 g *Mucuna*. These differences were highly significant.

TABLE 1

Clinical assessments; measures of parkinsonism on LD/DC, 15 g and 30 g *Mucuna pruriens*.

|  | LD/DC (SD) | 15 g *Mucuna* (SD) | 30 g *Mucuna* (SD) | Diff. LD/DC vs 15 g *Muc* | Diff. LD/DC vs 30 g *Muc* |
|---|---|---|---|---|---|
| Mean interpatient values: |  |  |  |  |  |
| UPDRS baseline | 49.8 (12.7) | 49.5 (15.3) | 46.9 (10.7) | n.s. | p = 0.046 |
| BRAIN baseline | 47.4 (11.0) | 44.0 (12.6) | 45.0 (13.6) | n.s. | n.s. |
| Best UPDRS "on" | 15.4 (8.0) | 15.5 (7.6) | 15.5 (8.5) | n.s. | n.s. |
| Best BRAIN "on" | 75.9 (18.4) | 78.5 (21.3) | 79.1 (15.0) | n.s. | n.s. |
| Mean intrapatient values: |  |  |  |  |  |
| Best UPDRS "on" | 0 | 0.125 | 0.125 | n.s. | n.s. |
| Best BRAIN "on" | 0 | +2.5 | +3.125 | n.s. | n.s. |
| Mean interpatient values*: |  |  |  |  |  |
| Time to full "on" | 68.5 (29.0) | 45.6 (30.4) | 34.6 (13.6) | p = 0.035 | p = 0.021 |
| Time to beginning of "on" | 54.6 (24.5) | 27.8 (14.1) | 23.0 (11.5) | p = 0.012 | p = 0.012 |
| Duration of full "on" | 167.4 (55.3) | 147.3 (30.5) | 204.5 (55.1) | n.s. | p = 0.021 |
| Mean intrapatient normalized values: |  |  |  |  |  |
| Duration of full "on" | 100% | 99% | 128% |  |  |

*values in minutes.
SD = Standard deviation.
LD/DC = L-Dopa/carbidopa.
BRAIN see Methods.
UPDRS refers to motor cores.

TABLE 2

Clinical assessments; dyskinesia measures on LD/DC, 15 g and 30 g Mucuna pruriens.

|  | LD/DC (SD) | 15 g Mucuna (SD) | 30 g Mucuna (SD) | Diff. LD/DC vs 15 g Muc | Diff. LD/DC vs 30 g Muc |
|---|---|---|---|---|---|
| Mean AIMS score | 8.0 (5.0) | 8.6 (4.9) | 8.0 (5.1) | p = 0.36 | p = 0.75 |
| Mean Goetz score | 2.0 (0.6) | 2.1 (0.6) | 1.9 (0.5) | p = 0.07 | p = 0.34 |
| Dyskinesia Monitor Index: |  |  |  |  |  |
| Mean interpatient index | 41.7 (12.1) | 39.7 (11.1) | 37.4 (6.1) | na | na |
| Mean intrapatient index | 0 | −1.98 | −4.32 | p = 0.16 | p = 0.27 |

SD = Standard Deviation
LD/DC = L-Dopa/carbidopa.

On an interpatient mean basis the duration of full "on"-status was 37 minutes (22%) longer on 30 g Mucuna compared with LD/DC. This difference was significant (p=0.021). The duration on 15 g mucuna was somewhat shorter than with LD/DC; by 20 minutes (12%). This difference was not significant supported by the normalized intrapatient evaluation (mean of % difference in individual patients) in which 15 g Mucuna reached 99% of the "on" time duration time of LD/DC. Although a difference in UPDRS scores at baseline reached significance for 30 g Mucuna versus LD/DC in the mean interpatient analysis, best UPDRS motor scores and tapping speed (BRAIN) when "on" did not differ significantly among the three study drugs.

The interrater reliability with respect to the rating of video recordings was satisfactory to good: Weighted kappa was 0.45 (p<0.0001) for Goetz scores (Spearman's rank 0.87, p<0.0001) and 0.62 (p<0.0001) for AIMS scores (Spearman's rank 0.97, p<0.0001). No significant differences in ratings were found among the study drugs. Since of one patient values were not listed due to a dislocation of the device during one session, the results with the Dyskinesia Monitor can only be evaluated for 7 patients. In spite of the significant differences in LD plasma levels, both the inter- and intrapatient DMI values did not differ significantly, but a dose dependent reduction in index values for Mucuna compared with LD/DC was recorded. Whether this reduction has a clinical basis needs to be further evaluated in view of the results with AIMS and Goetz.

EXAMPLE 4

Safety and Tolerability

Apart from the patient who dropped out due to vomiting during the intake of 30 g Mucuna and placebos, other adverse events were: mild and short-lasting nausea occurring in two patients on LD/DC and: in two patients on 30 g Mucuna, mild gastric pain in one patient on LD/DC, and mild dizziness in one patient each on LD/DC and on 15 g Mucuna. Total episodes were therefore 4 for LD/DC, 1 for 15 g and 2 for 30 g Mucuna. No clinically relevant changes in hematology and biochemistry parameters were observed.

IN VITRO STUDIES

EXAMPLE 5

Material and Methods of In Vitro Studies

Experimental Design:

Thirteen (13) different extracts of Mucana Pruriens were tested on the survival of primary cell cultures of mesencephalic neurons. Cell cultures were prepared from embryonic rodent mesencephalon on the $14^{th}$ day of gestation. Three or four concentrations of each extract were tested in triplicate in each paradigm, according to a previously published method (Mytilineou et al 1997, 1998). All experiments have been performed in a blinded fashion.

Extracts of Mucana Pruriens were tested for their effect on the following conditions:
  (I) Survival of cultured dopaminergic neurons
  (II) Survival of cultured dopamine neurons following exposure to:
    (a) depletion of GSH by buthionine sulfoximine (3 concentrations)
    (b) exposure to $MPP^+$ (3 concentrations)

Analysis of Data:

The effect of extracts of Mucana Pruriens on the survival of dopamine neurons were assessed by measuring:
  (a) the uptake of dopamine as a measure of the number of dopamine terminals and an index of the number of surviving dopamine neurons.
  (b) MTT (3-(4,5-dimethylthiazol-2-yl)-2,5-diphenyltetrazolium bromid) reduction as a measure of cell survival
  (c) LDH (lactate dehydrogenase) release as a measure of number of survival cells These techniques are well known to the person skilled in the art and have been published previously (Mytilineou et al 1997, 1998).

Miscellaneous Material: Pregnant rats are purchased from Taconic Farms (Germantown, N.Y.). Minimum essential medium (MEM) is obtained from GIBCO (Grand Isand, N.Y.), horse serum from Gemini (Calabasas, Calif.), and NU serum from Becton Dickinson (Bedford, Mass.). The Vectastain ABC Kit is form Vector Laboratories (Burlingame, Calif.). Other chemicals are purchased form Sigma (St. Louis, Mo.).

Cell Culture:

Mesencephalic cultures are prepared from rat embryos on gestational day 14 as previously described (Mytilineou et al 1993). Dissociated cells are plated on poly-l-omithine (0.1 mg/ml)-coated dishes (35 mm in diameter, Falcon) at a density of $10^5$ cells/$cm^2$. The feeding medium consists of MEM with 30 mM glucose, 2 mM glutamine, 10% horse serum and 10% NU serum (which contains 25% fetal calf serum and other additions).

Assay for Dopamine Uptake:

[$^3$H]DA uptake is determined as previously described (Hou et al. 1996). In brief, cultures are washed twice to remove residual drugs and incubated for 15 min in [$^3$H]DA (0.5 Ci/ml, 21.4 Ci/mmol). After two rinses and a 5 min incubation with fresh buffer, the accumulated [$^3$H]DA is extracted in 1 ml of 95% ethanol, added to 10 ml of Exoscint A and counted in a scintillation spectrometer.

MTT Assay:

Cell viability was determined by the MTT (3-(4,5-dimethylthiazol-2-yl)-2,5-diphenyltetrazolium bromid) reduction assay, as described previously (Han et al., 1996). In brief, 50 µl of a 5 mg/ml solution of MTT was added to each cell culture well containing 0.5 ml medians. After 3 hours incubation at 37° C. the medium was removed carefully and the formazan crystals formed were dissolved in 1 ml isopropyl alcohol by gently shaking of the plate. Absorbance was determined at 570 nm in a microplate reader.

LDH Assay:

A modification of the method by Bergmeyer et al. (1963) was used to determine LDH activity in the culture medium and the cells. Culture medium was collected, centrifuged to remove debris and frozen at −80° C. until assay. Cells were collected in 1.0 ml of 50 mM potassium phosphate buffer at pH 7.2, sonicated in the cold for 10 s and frozen at −80° C. 100 µl of supernatant and 100µl of NADH (1.2 mg/ml H$_2$O stock) were added to 800 µl of buffer and the samples were vortex-mixed. 250 µl aliquots (triplicates) were placed into 96-well plates at room temperature and the reaction was initiated by addition of 25 µl of sodium pyruvate (0.35 µg/ml H$_2$O stock). The rate of disappearance of NADH was measured at 340 nm on a plate reader (Spectramax™, Molecular Devices Corporation, Sunnyvale Calif.).

Statistical assessment:

For multiple comparisons, statistical analysis were carried out using an ANOVA followed by Tukey's or Dunnett's test. Significance between groups was tested with an independent two-tailed t-test.

Composition and Properties of Extracts:

1. M-HX1299 (50 mg): 200 g pulverised seed material of *Mucana pruriens* were shaken at room temperature in 200 ml n-hexane for 18 hours. After filtration, the material was further washed with 100 ml n-hexane and filtered. The filtrates were collected and the solvent distilled off to obtain a yellowish oil.
2. M-AC1299 (50 mg): The residue of the n-hexane extraction (was above), was shaken for 18 hours at room temperature in acetone (200 ml) and filtered. The residue was extracted once more with 200 ml acetone by further shaking for 18 hours and filtered. The residue was washed with acetone (100 ml) and filtered. After pooling, the filtrates were evaporated by distillation under reduced pressure yielding a yellowish mass.
3. M-W-EL1299 (50 mg): The residue (obtained from the above extractions, ca. 96 g) was shaken for 18 hours at room temperature in 500 ml of a mixture of water-EtOH, 1:1 with 0.5% ascorbic acid. The solvent was filtered and concentrated under reduced pressure at a temperature of 35° C. Above extraction procedure was repeated four times. After concentration, the filtrates were collected and the solvent removed under vacuum to get the solid mass.
4. M-CH1299 (50 mg): 100 g of the pulverised seed s of *M. pruriens* were shaken for 18 hours at room temperature in EtOH (100 ml). After filtration, the residue was again shaken for 18 hours and filtered. The process was repeated for a total of four extractions. The filtrates, were concentrated and pooled together to get the extract.
5. M-EL0100 (50 mg): 20 g of the pulverised seeds of *M. pruriens* were shaken for 18 hours at room temperature in EtOH (100 ml). After filtration, the residue was again shaken for 18 hours and filtered. The process was repeated for a total fo four extractions. The filtrates were concentrated and pooled together to get the extract.
6. M-W0100 (50 mg): The residue obtained from the ethanol extraction, as stated above, was further shaken for 18 hours at room temperature in demineralised water and filtered. The extraction was repeated for three times more. The filtrates were pooled together and water distilled off, after passing SO$_2$ to prevent the oxidation of L-DOPA. The solid sticky extract was thus obtained.
7. M-ML0100 (50 mg): 10 g of the pulverised seeds of *M. pruriens* were shaken for 18 hours at room temperature in methanol (50 ml) and filtered. The extraction of the residue was followed two more times with methanol and filtered. The filtrates were pooled together and the solvent distilled off to yield the semi-solid mass.
8. M-BL0100 (50 mg): 10 g of the pulverised seeds of *M. pruriens* were shaken for 18 hours at room temperature in n-butanol (50 ml) and filtered. The extraction of the residue was followed two more times with n-butanol and filtered. The filtrates were pooled together and the solvent distilled off. The oily extract was thus obtained.
9. M-PL0100 (50 mg): 10 g of the pulverised seeds of *M. pruriens* were shaken for 18 hours at room temperature in n-propanol (50 ml) and filtered. The extraction of the residue was again followed two more times with n-propanol and filtered. The filtrates were pooled together and the solvent distilled off to get an oily mass.
10. M-ACPL0800: The *M. pruriens* seed powder was defatted twice or 18 hrs at room temperature with acetone by shaking the powder each with 200 ml acetone, the combined solvent evaporated at reduced temperature and the residue extracted for 18 hrs at room temperature with 500 ml n-propanol and then evaporated to dryness. This extract contains traces (negligible) amounts of L-DOPA (in TLC detectable after enrichment only).
11. MWEL0700: The *M. pruriens* seed powder was not defatted with acetone, but directly extracted with a 1:1 mixture of water:ethanol without ascorbic acid addition by shaking 100 g powder with 50.0 ml of this solvent mixture for 18 hrs at room temperature. The solvent was evaporated at reduced temperatur to dryness. The extract contains L-DOPA in traces only.

| SOLUBILITY OF THE EXTRACTS | |
|---|---|
| 1. M-HX1299: | 6.5 mg in 0.5 ml DMSO + 0.5 ml dist. water |
| 2. M-AC 1299: | 2.0 mg in 6 drops of DMSO + 0.2 ml dist. water |
| 3. M-W-EL 1299: | 5.0 mg in 0.1 ml dist. Water |
| 4. M-CH1299: | 10.0 mg in 0.3 ml DMSO + 0.8 ml dist. water |
| 5. M-EL0100: | 3.0 mg in 2 drops DMSO + 1.0 ml dist. water |
| 6. M-W0100: | 7.0 mg in 0.4 ml warm (60° C.) dist. water |
| 7. M-ML0100: | 4.0 mg in 0.3 ml dist. water |
| 8. M-BL0100: | 7.0 mg in 4 drops DMSO + 0.4 ml dist. water |
| 9. M-PL0100: | 5.0 mg in 4 drops DMSO + 0.4 ml dist. water |
| 10. LAT543 | soluble in water in various concentrations, light opalescent |
| 11. LAT543-0 | soluble in water in various concentrations, light opalescent |

| L-DOPA COMPOSITION OF THE EXTRACTS | |
|---|---|
| 1. M-HX1299: | No L-DOPA content. |
| 2. M-AC1299: | No L-DOPA content. |
| 3. M-W-EL1299: | High L-DOPA content. |

-continued

| L-DOPA COMPOSITION OF THE EXTRACTS | |
|---|---|
| 4. M-CH1299: | No L-DOPA content. |
| 5. M-EL0100: | Moderate L-DOPA content. |
| 6. M-W0100: | High L-DOPA content. |
| 7. M-ML0100: | Moderately high L-DOPA content |
| 8. M-BL0100: | Moderate L-DOPA content. |
| 9. M-PL0100: | Trace of L-DOPA content. |
| 10. M-ACPL0800 | Trace of L-DOPA content. |
| 11. MWEL0700 | Trace of L-DOPA content. |
| 12. LAT543 | No L-DOPA content |
| 13. LAT543-0 | No L-DOPA content |

EXAMPLE 6

Extraction Procedure of *Mucuna Pruriens* Seeds, Fractionated Extraction

*Mucuna Pruriens* extracts were generated by performing steps 1 to 7 of the following protocol:

Extraction Procedures of *Mucuna pruriens* Seeds (Batch No. MU 99001)

1. Hexane extract (no. M-HX1299): 200 g pulverised seed material of *Mucuna pruriens* were shaken at room temperature in 200 ml n-hexane for 18 hrs. After filtration, the material was further washed with 100 ml n-hexane and filtered. The filtrates were collected and solvent distilled off to obtain a yellowish oily liquid (5.5 g) in a yield of 2.75% (w/w). The 50 mg extract gave clear solution in 1 ml DMSO (5% v/v).

2. Acetone extract (no. M-AC1299): The residue of the n-hexane extraction, was shaken for 18 hrs. at room temperature in acetone (200 ml) and filtered. The residue was extracted once more with 200 ml acetone by further shaking for 18 hrs. The residue was washed with acetone (100 ml) and filtered. After pooling, the filtrates were evaporated by distillation under reduced pressure yielding an yellowish mass (2.02 g) to a yield of 1.0% (w/w).

3. Water-Ethanol (1:1) extract (M-W-EL1299): The residue (ca. 96 g) was shaken for 18 hrs. at room temperature in 500 ml of a mixture of water, EtOH, 1:1 with 0.5% ascorbic acid. The solvent was filtered and concentrated under reduced pressure at a temperature of 35° C. Above extraction procedure was repeated four times. After concentration, the filtrates were collected and the solvent reduced to one tenth and kept at 2-4° C. for 24 hour. The crystallized matter was filtered and filtrate was kept for another 24 hours at 2-4° C. The crystallized matter was again filtered and taken together to get 1.75 g crystals in a yield of 1.75%. The filtrate was evaporated to dryness to get a solid mass (22.51 g) with 1.78 g as crude L-DOPA obtained after crystallization.

4. Chloroform extract (M-CH1299): 100 g of the pulverised seeds of *M. pruriens* were shaken for 18 hrs. at room temperature in 1.7% ammoniated chloroform (300 ml). The extract was filtered and the extraction was repeated three times. The concentrated extract was washed with water (100 ml) and further concentrated to afford 4.0 g extract in a yield of 4.0 (w/w).

5. Ethanol extract (M-EL0100): 20 g of the pulverised seeds of *M. pruriens* were shaken for 18 hrs. at room temperature in EtOH (100 ml). After filtration, the residue was again shaken for 18 hrs. and filtered. The process was repeated for a total of four extractions. The filtrates were concentrated and pooled together to get 1.34 g extract. The extract was tested for the presence of L-DOPA by TLC, positively.

6. Aqueous extract (M-W0100): The residue abtained from the ethanol extraction, as stated above, was further shaken for 18 hrs. at room temperature in demineralised water and filtered. The extraction was repeated for three times more. The filtrates were pooled together and water distilled off, after passing $SO_2$ to prevent the oxidation of L-DOPA. The extract (4.68 g) was tested for the presence of L-DOPA.

7. Acetone extract (M-AC0100): 10 g of the pulverised seeds of *M. pruriens* were shaken for 18 hrs. at room temperature in acetone (50 ml). After filtration, the residue was again extracted with acetone. The extraction was repeated three times more. The filtrates were pooled together and the solvent distilled off. The extract (0.37 g) was used for the presence of phosphatides.

EXAMPLE 7

Effect of Extracts on Primary Dopaminergic Cultures

Mesencephalic cultures were treated with different concentrations of extracts for 7 days. [$^3$H]Dopamine uptake was measured as an index of dopamine neuron survival and growth. This is a quantitative measurement that reflects the number of dopamine neurons and terminals.

The results of the extracts on native dopaminergic cultures are shown in table 3. Three extracts stimulated at a dose of 0.05 µg/ml. However, only one extract, M-PL0100, stimulated at all doses and significantly increased dopamine uptake in the cultures after one week of treatment. The effect was close to a 2-fold increase. However, the SEM (SEM=Structural Equation Modeling, a comprehensive statistical approach to testing hypotheses about relations among observed and latent variables (measured variables and unmeasured constructs) was quite high. Notably, no dose response was observed, possibly due to maximum effectiveness of the lowest concentration used (0.05 µg/ml). M-EL0100 and M-BL0100 showed a significant increase in uptake only at 0.05. µg/ml and LAT543-0 only at 50 µg/ml.

TABLE 3

Effect of *Mucana pruriens* extracts on the growth of dopamine neurons

| Compound | [$^3$H]Dopamine Uptake (% of Control) | | | |
|---|---|---|---|---|
| (µg/ml) | 0.05 | 0.5 | 5 | 50 |
| M-HX1299 | 124.9 ± 10.2 | 106.0 ± 11.2 | 92.9 ± 9.7 | 100.5 ± 13.3 |
| M-AC1299 | 115.4 ± 9.0 | 95.4 ± 8.9 | 93.1 ± 9.3 | 121.7 ± 7.1 |

TABLE 3-continued

Effect of *Mucana pruriens* extracts on the growth of dopamine neurons

| Compound | [³H]Dopamine Uptake (% of Control) | | | |
|---|---|---|---|---|
| (μg/ml) | 0.05 | 0.5 | 5 | 50 |
| M-W-EL1299 | 127.8 ± 10.4 | 111.1 ± 6.8 | 109.1 ± 7.5 | 100.5 ± 12.8 |
| M-CH1299 | 129.5 ± 18.1 | 115.8 ± 12.7 | 105.3 ± 8.1 | 101.9 ± 9.0 |
| M-EL0100 | 184.9 ± 20.3* | 146.5 ± 14.9 | 127.8 ± 12.5 | 140.8 ± 12.5 |
| M-W0100 | 120.8 ± 9.4 | 102.7 ± 8.9 | 103.3 ± 13.3 | 86.3 ± 11.2 |
| M-ML0100 | 122.9 ± 13.4 | 119.5 ± 8.3 | 115.3 ± 13.1 | 106.4 ± 10.0 |
| M-BL0100 | 139.1 ± 19.4* | 108.3 ± 9.9 | 89.4 ± 6.7 | 130.1 ± 9.3 |
| M-PL0100 | 206.3 ± 30.4* | 187.7 ± 20.3* | 170.1 ± 21.3* | 191.6 ± 24.5* |
| LAT543 | 135.1 ± 26.5 | 108.6 ± 14.2 | 117.6 ± 16.3 | 105.6 ± 10.2 |
| LAT543-0 | 139.1 ± 19.4 | 117.9 ± 8.6 | 120.4 ± 12.4 | 156.2 ± 14.6* |
| MACPL0800 | — | — | — | — |
| MWEL0700 | — | — | — | — |

*p < 0.05 ANOVA followed by Dunnett multiple comparison test

EXAMPLE 8

Effect of Extracts in Protecting Mesencephlic Cultures from the Toxic Effects of MPP[30]

Mesencephlic cultures were treated with 5 μM MPP+ for 24 hours in the absence or presence of different concentrations of extracts. [³H]Dopamine uptake was measured 48 hours after removing MPP+ (table 4). Four compounds protected dopamine neurons from MPP+ toxicity (M-W-EL1299; M-W0100 and MWEL0700). All were effective at a concentration of 50 μg/ml.

TABLE 4

Effect of *Mucuna pruriens* extracts on the toxicity of MPP+ to dopamine neurons

| Extract | [³H]Dopamine Uptake (% of no MPP+) | | | |
|---|---|---|---|---|
| (μg/ml) | 0 | 0.5 | 5 | 50 |
| M-HX1299 | 25.7 ± 2.5 | 27.4 ± 2.6 | 30.1 ± 3.7 | 27.3 ± 2.5 |
| M-AC1299 | 31.4 ± 3.6 | 37.9 ± 4.4 | 35.5 ± 3.2 | 34.9 ± 2.7 |
| M-W-EL-1299 | 25.5 ± 2.5 | 31.3 ± 3.8 | 33.2 ± 3.3 | 63.1 ± 5.7 |
| M-CH1299 | 31.3 ± 1.7 | 32.6 ± 3.1 | 29.1 ± 3.1 | 34.3 ± 2.2 |
| M-EL0100 | 34.6 ± 6.0 | 33.0 ± 5.3 | 40.0 ± 5.8 | 47.2 ± 8.0 |
| M-W0100 | 39.1 ± 3.7 | 52.0 ± 4.1 | 50.8 ± 2.5 | 59.6 ± 4.6 |
| M-ML0100 | 28.8 ± 2.0 | 23.7 ± 1.2 | 32.9 ± 2.4 | 50.7 ± 2.4 |
| M-BL0100 | 36.0 ± 4.0 | 32.8 ± 4.6 | 34.7 ± 4.9 | 36.5 ± 3.4 |
| M-PL0100 | 30.6 ± 4.6 | 31.6 ± 3.9 | 31.2 ± 4.7 | 40.4 ± 4.6 |
| LAT543 | 30.2 ± 3.0 | 31.8 ± 3.9 | 34.7 ± 7.2 | 30.4 ± 4.6 |
| LAT543-0 | 28.9 ± 1.4 | 28.3 ± 2.6 | 27.3 ± 2.1 | 33.7 ± 1.1 |

TABLE 4-continued

Effect of *Mucuna pruriens* extracts on the toxicity of MPP+ to dopamine neurons

| Extract | [³H]Dopamine Uptake (% of no MPP+) | | | |
|---|---|---|---|---|
| (μg/ml) | 0 | 0.5 | 5 | 50 |
| MACPL0800 | — | — | — | — |
| MWEL0700 | 37.4 ± 2.8 | 36.4 ± 3.2 | 49.1 ± 3.4 | 78.6 ± 8.6 |

*Significance p < 0.05 or greater; ANOVA followed by Tukey-Kramer multiple comparisons test.

EXAMPLE 9

Effect of Extracts in Protecting Mesencephalic Cultures from the Toxic Effects of BSO Mesencephalic cultures were treated with 10 or 50 μM BSO for 72 hours to reduce GSH levels and cause oxidative damage. The extracts were added at the same time as the BSO. The MTT assay was performed to determine cell viability (table 5). As GSH depletion is toxic to all cells, the protection by the extracts in this assay is not necessarily restricted to dopamine neurons.

The LDH assay (table 6) was performed in the medium collected from the cultures and is a measure of cell viability. As this is a non-specific assay, protection by the extracts may not be restricted to dopamine neurons. In the studies, protection against MPP+ toxicity with both the MTT and LDH methods was observed for M-W-EL1299; M-ML0100, and MWEL0700.

TABLE 5

Effect of *Mucuna pruriens* extracts on toxicity of GSH depletion (MTT assay)

| | MTT Reduction (absorbance at 550) | | | | | |
|---|---|---|---|---|---|---|
| BSO (μM) | 0 | | 10 | | 50 | |
| Extract (50 μg/ml) | − | + | − | + | − | + |
| M-HX1299 | 1.60 ± 0.01 | 1.59 ± 0.03 | 1.31 ± 0.04 | 0.23 ± 0.05*** | 0.76 ± 0.04 | 0.05 ± 0.01*** |
| M-AC1299 | 1.55 ± 0.02 | 1.58 ± 0.02 | 1.42 ± 0.06 | 0.15 ± 0.02*** | 0.83 ± 0.05 | 0.03 ± 0.00*** |
| M-W-EL1299 | 1.68 ± 0.11 | 1.74 ± 0.08 | 1.52 ± 0.07 | 1.77 ± 0.09 | 1.02 ± 0.06 | 1.81 ± 0.11 |
| M-CH1299 | 1.88 ± 0.03 | 1.95 ± 0.02 | 1.10 ± 0.12 | 0.04 ± 0.00*** | 0.55 ± 0.07 | 0.01 ± 0.00*** |
| M-EL0100 | 1.97 ± 0.03 | 1.95 ± 0.03 | 1.36 ± 0.02 | 0.81 ± 0.04* | 0.65 ± 0.09 | 0.11 ± 0.02*** |
| M-W0100 | 1.26 ± 0.01 | 1.14 ± 0.04 | 1.05 ± 0.06 | 0.70 ± 0.02* | 0.66 ± 0.07 | 0.54 ± 0.05 |
| M-ML0100 | 1.81 ± 0.05 | 1.84 ± 0.06 | 1.48 ± 0.07 | 1.80 ± 0.05** | 0.84 ± 0.08 | 1.83 ± 0.05*** |

TABLE 5-continued

Effect of *Mucuna pruriens* extracts on toxicity of GSH depletion (MTT assay)

| | MTT Reduction (absorbance at 550) | | | | | |
|---|---|---|---|---|---|---|
| BSO (μM) | 0 | | 10 | | 50 | |
| Extract (50 μg/ml) | − | + | − | + | − | + |
| M-BL0100 | 1.22 ± 0.03 | 1.32 ± 0.00 | 1.17 ± 0.06 | 0.83 ± 0.12 | 0.91 ± 0.15 | 0.12 ± 0.02*** |
| M-PL0100 | 1.12 ± 0.02 | 1.07 ± 0.02 | 1.04 ± 0.02 | 0.31 ± 0.05*** | 0.64 ± 0.04 | 0.03 ± 0.01*** |
| LAT543 | 1.34 ± 0.05 | 1.55 ± 0.01 | 1.20 ± 0.17 | 0.82 ± 0.16** | 0.67 ± 0.16 | 0.08 ± 0.01* |
| LAT543-0 | 1.67 ± 0.02 | 1.68 ± 0.02 | 1.24 ± 0.07 | 0.49 ± 0.03*** | 0.52 ± 0.05 | 0.09 ± 0.01*** |
| MACPL0800 | 1.72 ± 0.03 | 1.64 ± 0.03 | 1.20 ± 0.10 | 0.30 ± 0.04*** | 0.56 ± 0.10 | 0.05 ± 0.02*** |
| MWEL0700 | 1.65 ± 0.03 | 1.73 ± 0.02 | 1.04 ± 0.05 | 1.71 ± 0.02*** | 0.61 ± 0.03 | 1.72 ± 0.04*** |

TABLE 6

Effect of *Mucuna pruriens* extracts on toxicity of GSH depletion (LDH assay). The stars in the tables relate to the legends. (p-values).

| | LDH released | | | | | |
|---|---|---|---|---|---|---|
| BSO (μM) | 0 | | 10 | | 50 | |
| Extract (50 μg/ml) | − | + | − | + | − | + |
| M-HX1299 | 7.8 ± 0.2 | 8.0 ± 0.4 | 20.8 ± 0.8 | 77.9 ± 3.3*** | 48.0 ± 1.7 | 75.0 ± 4.6*** |
| M-AC1299 | 6.9 ± 0.3 | 6.6 ± 0.2 | 9.1 ± 0.8 | 53.7 ± 4.7*** | 37.1 ± 1.9 | 60.6 ± 0.6*** |
| M-W-EL1299 | 5.2 ± 0.4 | 4.9 ± 0.9 | 11.9 ± 1.7 | 4.8 ± 0.9*** | 27.9 ± 5.0 | 4.8 ± 1.0*** |
| M-CH1299 | 6.9 ± 0.2 | 6.4 ± 0.2 | 37.6 ± 4.7 | 66.2 ± 1.2*** | 52.1 ± 2.2 | 69.5 ± 2.0* |
| M-EL0100 | 7.2 ± 0.2 | 6.4 ± 0.1 | 28.7 ± 1.2 | 49.4 ± 0.6*** | 50.2 ± 1.4 | 67.7 ± 1.7* |
| M-W0100 | 3.4 ± 0.1 | 5.9 ± 0.6 | 15.0 ± 2.2 | 19.4 ± 0.9 | 27.6 ± 2.4 | 27.5 ± 2.0 |
| M-ML0100 | 8.4 ± 0.4 | 8.0 ± 0.3 | 20.9 ± 1.9 | 7.7 ± 0.4*** | 47.7 ± 2.8 | 8.7 ± 0.3*** |
| M-BL0100 | 4.2 ± 0.2 | 4.6 ± 0.4 | 8.7 ± 1.1 | 23.6 ± 4.2** | 20.4 ± 4.5 | 43.9 ± 1.4*** |
| M-PL0100 | 7.3 ± 0.1 | 7.4 ± 0.5 | 10.0 ± 0.5 | 47.3 ± 2.8*** | 21.4 ± 5.4 | 54.8 ± 1.1*** |
| LAT543 | 3.9 ± 0.2 | 4.5 ± 0.3 | 13.6 ± 5.8 | 29.4 ± 3.9** | 37.2 ± 5.6 | 45.1 ± 1.0 |
| LAT543-0 | 7.2 ± 0.8 | 7.5 ± 0.7 | 28.1 ± 3.9 | 64.9 ± 2.1*** | 59.9 ± 2.9 | 76.3 ± 2.7* |
| MACPL0800 | 7.0 ± 0.6 | 6.0 ± 0.5 | 31.4 ± 6.2 | 64.7 ± 1.8*** | 57.0 ± 5.0 | 70.8 ± 1.0* |
| MWEL0700 | 7.3 ± 0.5 | 7.3 ± 0.6 | 41.6 ± 2.1 | 7.5 ± 0.8*** | 57.2 ± 1.6 | 8.9 ± 0.7*** |

Lactate dehydrogenase (LDH) is a cellular enzyme which is released from damaged or dying cells. Therefore, LDH values increase in case of cellular distress/damage. A strong increase after BSO addition is to be expected to the resulting GSH depletion. Without BSO the extracts did not increase LDH, indicating no toxic effects of the extracts themselfs. With BSO and with increasing dose LDH levels increase strongly with the exception of 3 extracts where LDH is maintained at the o level indicating strong protection. Remarkably, a number of extracts show a rise of LDH levels, indicating increased toxicity. All those extracts contain DMSO which in high concentrations may be toxic. It is likely that in this model DMSO potentiated the BSO toxicity. A similar phenomenon can be seen in table 5.

Something similar may be the case in the stimulation model (table 3). Three extracts stimulate with a dose of 0.05 μg/ml. Only M-PLO100 with all doses. All three extracts are alcohol extracts, however, only PL0100 does not contain DMSO and only a trace L-Dopa, the other two extracts contain DMSO and moderate L-Dopa concentration. Thus, it is possible that with increasing doses DSMO and/or L-Dopa (alone or in synergy) have a toxic effect and thereby undo the stimulatory effect.

REFERENCES (1) Manyam B. Paralysis agitans and levodopa in "Ayurveda": ancient Indian treatise. Mov Disord 1990; 5:47-48.

(2) Manyam B, Sanchez-Ramos JR. traditional and complementary therapies in Parkinson's Disease. Adv Neurol 1999; 80:565-5574.

(3) Damodaran M, Ramswamy R. Isolation of L-dopa from the seeds of *Mucuna pruriens*. Biochem 1937; 31:2149-2451.

(4) HP-200 in Parkinson's Disease Study Group. An alternative medicine treatment for Parkinson's Disease: results of a multicentre clinical trial. J Altern Complement Med 1995; 1:249-255.

(5) Vaidya A B, Rajgopalan T S, Mankodi N A, et al. Treatment of Parkinson's Disease with the Cowhage plant-*mucuna pruriens* (Bak). Neurology India 1978; 36:171-176.

(6) Nagashayana N. Sankarankutty P, Nampoothirir M R, Mohan P K, Mohankurrar K P. Association of L-dopa with recovery following ayuerveda medication in Parkinson's Disease. J Neurol Sci 2000; 176:124-127.

(7) Vaidya A B et al. The Inhibitory effect of the Cowhage Plant-*Mucuna pruriens*- and L-Dopa on Chlorpromazine-induced hyperprolactinaemia in man. Neurol India, 1978b; 26:177-182

(8) Hussain G, Manyam B V. *Mucuna pruriens* Proves More Effective than L-Dopa in Parkinson's Disease Animal Model: Phytotherapy Research, Vol 11, 419-423 (1997)

(9) Gibb W R G, Lees A J. The relevance of the Lewy body to the pathogenesis of idiopathic Parkinson's Disease. J Neurol Neurosurg Psychiatry 1988; 51:745-752.

(10) Folstein M F, Folstein S E, McHugh P R. "Mini-mental state". A practical method for grading the cognitive state of patients for the clinician. J Psychiatr Res 1975; 12:189-198.

(11) Giovanni G, van Schalkwijk J, Fritz V U, Lees A J. Bradykinesia akinesia inco-ordination test (BRAIN TEST): an objective computerised assessment of upper limb motor function. J Neurol Neurosurg Psychiatry 1999; 67:624-629.

(12) Duriff, Vidailhet M, Debilly B, Agid Y. Worsening of levodopa-induced dyskinesias by motor and mental tasks [In Process Citation]. Mov Disord 1999; 14-242-245.

(13) Manson A J. Brown P, O'Sullivan J D, Asselman P, Buckwell D, Lees A J. An ambulatory dyskinesia monitor. J Neurol Neurosurg Psychiatry 2000; 68. 196-201.

(14) Mars H. modification of levodopa effect by systemic decarboxylase inhibition. Arch Neurol 1973; 28:91-95.

(15) Jaffe M. Clinical studies of carbidopa and L-dopa in the treatment of Parkinson's Disecase. Adv Neurol 1973; 2:161-172.

(16) Pinder R M, Brogden R N, Sawyer P R, Speight T M, Avery G S. Drugs 1976; 11:329-377.

(17) Cedarbaum J M, Kutt H, Dhar A K, Watkins S, McDowell F H. Effect of supplenmental carbidopa on bioavailability of L-dopa. Clin Neuropharmacol 1986; 9:153-159.

(18) Berg mark J. Carlsson A; granerus A K, Jagenburg R. Magrusson T, Svanborg A. Decarboxylation of orally administered L-dopa in the human digestive tract. Naunyn-Schmiedebergs Archives of pharmacology 1972; 272,-437.

(19) Bakke O M, Scheline R R. Inhibition of a minor pathway of L-dopa metabolism in the intestinal lumen using a decarboxylase inhibitor (Ro 4-4602). J Pharmacy Pharmacol 1974; 26:377.

(20) Pletscher A, Bartholini G. Selective raise in brain dopamine by inhibition of extracerebral levodopa decarboxylation. Clin Pharm Ther 1971; 12:117-131.

(21) Dunner D L, Brodie K H, Goodwin F K. Plasma dopak response to levodopa administration in man: effects of a peripheral decarboxylase inhibitor. Clin Pharm Ther 1971; 12:212.

(22) Bianchine J R, Messiha F S, Hsu T H. Peripheral aromatic amino acid decarboxylase inhibitor in parkinsonism. II. Effect on metabolism of L-2-$_{14}$C-dopa. Clin Pharm Ther 1972; 13:584-594.

(23) Pappert E J, Buhrfiend C, Lipton J W, Carvey P M, stebbins G T, Goetz C G. Levodopa stability in solution: time course, environmental effects, and practical recommendations for clnical use. Mov Disord 1997; 11:24-26.

(24) Yazawa I; Terao Y, Hashimoto K, Sakuta M. Gastric acid secretion and absorption of levodopa in patients with Parkinson's Disease—the effect of supplement therapy to gastric acid. Rinsho Shinkeigaku 1994; 34:264-266.

(25) Reid J L, Caine D B, Vakil S D, Allen J G, Davies C A. Plasma concentrations of levodopa in parkinsonism before and after inhibition of peripheral decarboxylase. J Neurol Sci 1972; 17:45-51.

(26) Rinne U K, Sonninen V, Sirtola T. Plasma concentration of levodopa in patients with Parkinson's Disease. Europ Neurol 1973; 10:301-310.

(27) Nutt J G. Levodopa-induced dyskinesia: review, observations, and speculations. Neurology 1990; 40:340-345.

(28) Kempster P A, Bogetic Z, et al. Motor effects of broad beans (*Vicia fava*) in Parkinsori's Disease: single dose studies. Asia Pacific J Clin Nutr 1993; 2:85-89.

(29) Melvin E, Daxenbichler C H, Etten V, Fontaine R E, Talletn W H. L-dopa recovery from *Mucuna* seed. J Agr Food Chem 1972; 20:1046-1048.

(30) Tripathi Y B, Upadhyay A K. Effect of the alcohol extract of the seeds of *Mucuna pruriens* on free radicals and oxidative stress in albino rats. Phytother Res 2002; 16:534-538.

The invention claimed is:

1. A method of preparing an extract or extract fraction of *Mucuna pruriens* seeds comprising:
    extracting a seed of *Mucuna pruriens* with n-hexane to provide a first extract solution;
    filtering the first extract solution to provide a first filter retentate;
    extracting the first filter retentate with acetone to provide a second extract solution;
    filtering the second extract solution to provide a second filter retentate;
    extracting the second filter retentate with an approximately 1:1 mixture of water and ethanol containing approximately 0.5% ascorbic acid to provide third extract solution;
    filtering the third extract solution to provide a third filter retentate;
    repeating the extraction with an approximately 1:1 mixture of water and ethanol containing approximately 0.5% ascorbic acid at least four times using the third through a sixth filter retentate to provide a fourth through seventh extract solutions;
    pooling at least two of the extract solutions to provide a pooled extract solution; and
    concentrating the pooled extract solution to form an extract or extract fraction containing at least one pharmaceutically active component, substance, fraction, or mixture thereof.

2. The method of claim 1, further comprising solubilizing the extract or extract fraction in a solvent comprising DMSO, distilled water, or a mixture thereof.

3. The method of claim 1, further comprising formulating the extract or extract fraction in a form selected from the group consisting of comminuted form, as granules, powder, precipitate, dried extract, exudate, and any combinations thereof.

4. The method of claim 1, further comprising formulating the extract or extract fraction for oral application, topical application or parenteral application.

5. The method of claim 1, further comprising preparing a formulation selected from the group consisting of an infusion solution, an injection solution, an orally administrable form, a gelatin-capsule, a tablet, a controlled release tablet, a granulate, a food supplement, an enema, and any combinations thereof.

6. The method of claim 1, wherein the component, substance, fraction, or mixture thereof does not contain a pharmaceutically effective amount of L-dopa.

7. The method of claim 1, wherein the extract or extract fractions further comprises at least one additional pharmaceutically active agent.

* * * * *